United States Patent
Abbadasari et al.

(10) Patent No.: US 11,823,107 B1
(45) Date of Patent: *Nov. 21, 2023

(54) DISPLAY OF HOSPITAL TRANSPORT INFORMATION ON A PORTABLE DEVICE

(71) Applicant: TeleTracking Technologies, Inc., Pittsburgh, PA (US)

(72) Inventors: Ranjit Abbadasari, Pittsburgh, PA (US); Harold Barrett, Greensburg, PA (US); Jason Harber, Pittsburgh, PA (US); Abhay Jaiswal, Pittsburgh, PA (US); Tom Perry, Dubois, PA (US)

(73) Assignee: TELETRACKING TECHNOLOGIES, INC., Pittsburgh, PA (US)

(*) Notice: Subject to any disclaimer, the term of this patent is extended or adjusted under 35 U.S.C. 154(b) by 195 days.

This patent is subject to a terminal disclaimer.

(21) Appl. No.: 17/129,178

(22) Filed: Dec. 21, 2020

Related U.S. Application Data

(63) Continuation of application No. 15/642,716, filed on Jul. 6, 2017, now Pat. No. 10,885,484, which is a
(Continued)

(51) Int. Cl.
*G06Q 10/0633* (2023.01)
*G06Q 10/0631* (2023.01)
(Continued)

(52) U.S. Cl.
CPC ... *G06Q 10/0633* (2013.01); *G06Q 10/06311* (2013.01); *G06Q 10/1097* (2013.01); *G06Q 50/22* (2013.01)

(58) Field of Classification Search
CPC ........ G06Q 10/0633; G06Q 10/06311; G06Q 10/1097; G06Q 50/22; G16H 40/20; G16H 40/67
(Continued)

(56) References Cited

U.S. PATENT DOCUMENTS

| 8,549,600 B2 | 10/2013 | Shedrinsky |
| 2006/0167738 A1* | 7/2006 | Spear ............ G06Q 10/063114 340/539.13 |

(Continued)

FOREIGN PATENT DOCUMENTS

WO WO-2013109717 A1 * 7/2013 ....... G06Q 10/06311

OTHER PUBLICATIONS

Victor Gonzalez; Context-aware mobile communication in hospital; 2003, IEEE Computer (Year: 2003).*

(Continued)

*Primary Examiner* — Hiep V Nguyen
(74) *Attorney, Agent, or Firm* — FERENCE & ASSOCIATES LLC

(57) ABSTRACT

An aspect provides a method, including: communicating, to the hospital transport management system, information sufficient to authenticate a user of the handheld portable information handling device; obtaining available hospital transport job information from the hospital transport management system; displaying information related to the available hospital transport job; displaying functional display icons comprising an accept job icon and a bypass job icon; communicating acceptance information of the authenticated user for an available hospital transport job to the hospital transport management system; and displaying a status of the accepted job and icons for changing a status of the accepted job by the transporter.

17 Claims, 27 Drawing Sheets

Related U.S. Application Data continuation of application No. 13/843,542, filed on Mar. 15, 2013, now Pat. No. 9,704,117.

(51) Int. Cl.
  *G06Q 10/1093* (2023.01)
  *G06Q 50/22* (2018.01)

(58) Field of Classification Search
  USPC .......................................................... 705/2
  See application file for complete search history.

(56) References Cited

U.S. PATENT DOCUMENTS

| | | | |
|---|---|---|---|
| 2009/0254365 A1* | 10/2009 | Gravina | G16H 40/63 |
| | | | 715/777 |
| 2012/0035945 A1 | 2/2012 | Jain et al. | |
| 2013/0065628 A1 | 3/2013 | Pfeffer | |
| 2013/0204633 A1* | 8/2013 | Jourdan | G16H 40/20 |
| | | | 705/2 |

OTHER PUBLICATIONS

Manion, R; Transport Provision and Mobility Assistance for Disabled People: A Consumer Evaluation of Planning and Practice; The University of Manchester (United Kingdom), ProQuest Dissertations Publishing, 1993. 29405305 (Year: 1993).*

* cited by examiner

Assignment

FIG. 7 Job List – Supervisor with self-dispatch, collapsed (left), Transporter with self-dispatch expanded (right).

FIG. 8 Job Details – Transport Job, regular (left), assist job (right)

FIG. 9   Outpatient Job (left), Job with Special Instructions (right)

Batch Item Job

Job Status - Available  FIG. 11

Processing (left), Retrieving new job (right)

Select Mode of Travel

Messages UI – normal (left), edit mode (right)

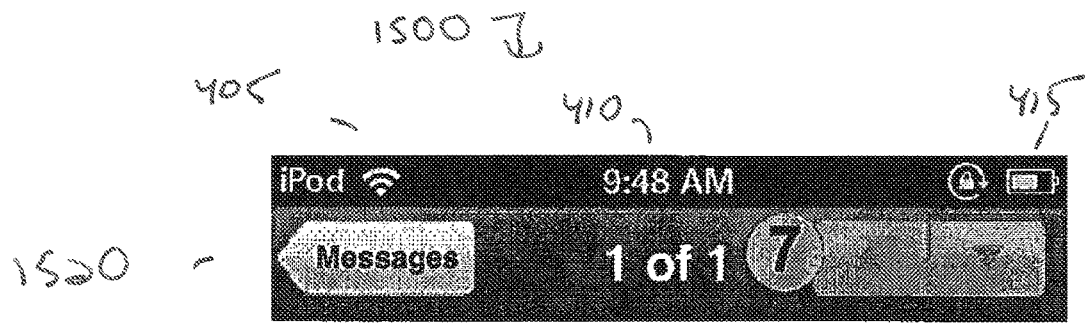
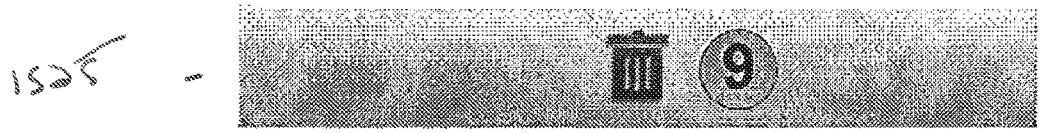
FIG. 15
Messages UI – Edit Mode

Transporter Break

Record Mini Task

Request Assistance

FIG. 19 Release Self – Job Details button (left), Release Self screen (right)

Create Roundtrip

Reschedule Job

Delay Job – no reason code (left), reason code required (right)

FIG. 23 Resume Job – Job Details button (left), Resume Job screen (right)

Cancel Job – no reason code (left),
reason code required (right)

DISPLAY OF HOSPITAL TRANSPORT INFORMATION ON A PORTABLE DEVICE

CROSS REFERENCE TO RELATED APPLICATIONS

This application is a continuation application of co-pending U.S. patent application Ser. No. 15/642,716, entitled "DISPLAY OF HOSPITAL TRANSPORT INFORMATION ON A PORTABLE DEVICE," and filed on Jul. 6, 2017, which is a continuation application of U.S. Pat. No. 9,704,117, entitled "DISPLAY OF HOSPITAL TRANSPORT INFORMATION ON A PORTABLE DEVICE,", filed on Mar. 15, 2013, and issued on Jul. 11, 2017, the contents of all of which are hereby incorporated by reference in their entirety.

BACKGROUND

It is not unusual for hospital patients not to be ambulatory and to need assistance to move from one part of the hospital facility to another. Hospital staff who assist patients in moving from one part of the facility are generally referred to as transporters. There are many more patients in a hospital than there are transporters and transporters need to be dispatched to patients who need transport. Dispatch is generally accomplished manually through human intervention or through the use of an alphanumeric pager carried by the transporter.

BRIEF SUMMARY

In summary, one aspect provides a method, comprising: at an application of a handheld portable information handling device with a touch screen display, wherein the application displays a plurality of user interfaces, each of the plurality of user interfaces having a subset of information corresponding to a hospital transport management system: communicating, to the hospital transport management system, information sufficient to authenticate a user of the handheld portable information handling device within the hospital transport management system, wherein the user comprises a transporter, wherein, upon authentication, the application displays the plurality of user interfaces of the hospital transport management system at the handheld portable information handling device; obtaining available hospital transport job information from the hospital transport management system comprising information for all available transport jobs; displaying, to the transporter within one of the plurality of interfaces, the available hospital transport job information for a subset of the all available transport jobs, wherein the subset comprises available hospital transport job information based upon a current status of the transporter; displaying, in response to the transporter selecting an available hospital transport job within one of the plurality of interfaces, information related to the available hospital transport job; displaying, within one of the plurality of interfaces, functional display icons comprising an accept job icon and a bypass job icon; communicating, in response to user interface with the accept job icon, acceptance information of the authenticated user for an available hospital transport job to the hospital transport management system, wherein the hospital transport management system modifies details of the available hospital transport job within the hospital transport management system upon receipt of the acceptance information, the modified details being viewable by other users of the hospital transport management system; and displaying, within one of the plurality of interfaces and to the transporter, a status of the accepted job and icons for changing a status of the accepted job by the transporter.

Another aspect provides a portable handheld information handling device, comprising: a touch screen display; one or more processors; an application displaying a plurality of user interfaces, each of the plurality of user interfaces having a subset of information corresponding to a hospital transport management system; a memory operatively coupled to the one or more processors that stores instructions executable by the one or more processors to perform acts comprising: at an application of a handheld portable information handling device with a touch screen display, wherein the application displays a plurality of user interfaces, each of the plurality of user interfaces having a subset of information corresponding to a hospital transport management system: communicating, to the hospital transport management system, information sufficient to authenticate a user of the handheld portable information handling device within the hospital transport management system, wherein the user comprises a transporter, wherein, upon authentication, the application displays the plurality of user interfaces of the hospital transport management system at the handheld portable information handling device; obtaining available hospital transport job information from the hospital transport management system comprising information for all available transport jobs; displaying, to the transporter within one of the plurality of interfaces, the available hospital transport job information for a subset of the all available transport jobs, wherein the subset comprises available hospital transport job information based upon a current status of the transporter; displaying, in response to the transporter selecting an available hospital transport job within one of the plurality of interfaces, information related to the available hospital transport job; displaying, within one of the plurality of interfaces, functional display icons comprising an accept job icon and a bypass job icon; communicating, in response to user interface with the accept job icon, acceptance information of the authenticated user for an available hospital transport job to the hospital transport management system, wherein the hospital transport management system modifies details of the available hospital transport job within the hospital transport management system upon receipt of the acceptance information, the modified details being viewable by other users of the hospital transport management system; and displaying, within one of the plurality of interfaces and to the transporter, a status of the accepted job and icons for changing a status of the accepted job by the transporter.

A further aspect provides a program product, comprising: a storage device having computer program code embodied therewith, the computer program code being executable by a processor and comprising: computer program code configured to communicate to the hospital transport management system, information sufficient to authenticate a user of the handheld portable information handling device within the hospital transport management system, wherein the user comprises a transporter, wherein the handheld portable information handling device comprises a touch screen display and an application displaying a plurality of user interfaces, each of the plurality of user interfaces having a subset of information corresponding to a hospital transport management system, wherein, upon authentication, the application displays the plurality of user interfaces of the hospital transport management system at the handheld portable information handling device; computer readable program code configured to obtain available hospital transport job information from the hospital transport management system comprising information for all available transport jobs; computer readable program code configured to display, to the transporter within one of the plurality of interfaces, the available hospital transport job information for a subset of the all available transport jobs, wherein the subset comprises available hospital transport job information based upon a current status of the transporter; computer readable program code configured to display, in response to the transporter selecting an available hospital transport job within one of the plurality of interfaces, information related to the available hospital transport job; computer readable program code configured to display, within one of the plurality of interfaces, functional display icons comprising an accept job icon and a bypass job icon; computer readable program code configured to communicate, in response to user interface with the accept job icon, acceptance information of the authenticated user for an available hospital transport job to the hospital transport management system, wherein the hospital transport management system modifies details of the available hospital transport job within the hospital transport management system upon receipt of the acceptance information, the modified details being viewable by other users of the hospital transport management system; and computer readable program code configured to display, within one of the plurality of interfaces and to the transporter, a status of the accepted job and icons for changing a status of the accepted job by the transporter.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 15 illustrates an exemplary user interface for viewing a message sent to the user in some embodiments.

DETAILED DESCRIPTION

Figure 1:
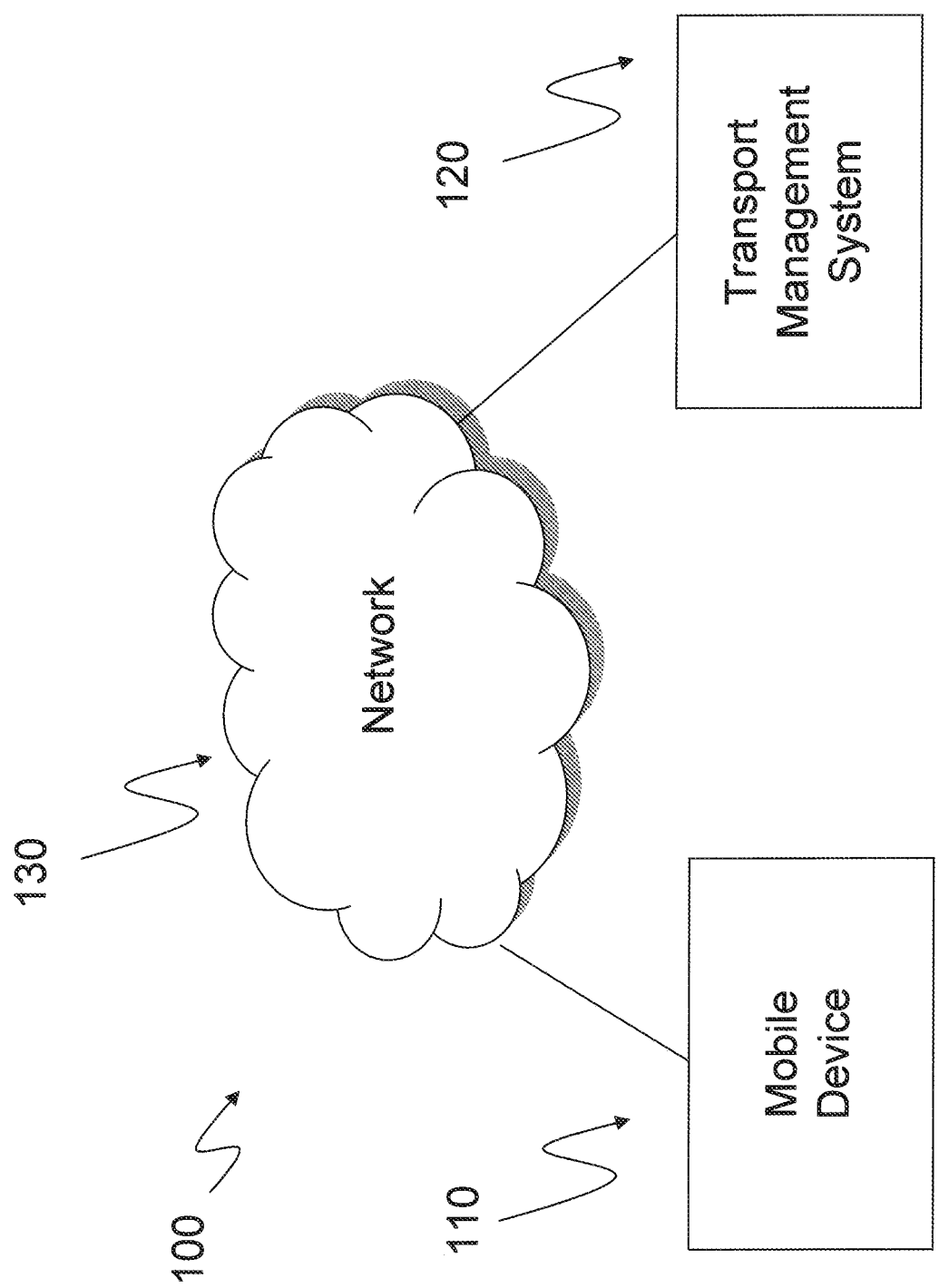
FIG. 1 illustrates certain selected components of a hospital information network.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As portable electronic devices have become more compact and the number of functions performed by a given device increases, it has become a significant challenge to design a user interface that allows users to easily interact with a multifunction device. This challenge is particularly significant for handheld portable devices, which have much smaller screens than desktop or laptop computers.

It is presently preferred that an application be placed on the handheld portable device which runs through a browser. Examples of appropriate handheld portable devices include iPods and smart phones. (IPOD is a trademark of Apple Corporation.) Any suitable handheld portable electronic device may be used. Running through a browser permits the application to run independent of the operating system used on the mobile device, although an operating specific application may also be utilized. The application may be programmed in any number of suitable computer languages, however, it is currently preferred to be programmed in C #, although any suitable programming language may be used. As discussed below, the application may take advantage of the hardware of the mobile device to operatively connect to a Transport Management System. The application may obtain data from the Transport Management System, updated periodically, or a Transport Management System may push certain data to the mobile device.

Doing so permits the information being displayed on the portable handheld device (or other similar device) to be organized in a manner that is effective in conveying the information to the user of the portable handheld device. Moreover, as a portable handheld device remains with a member of staff, the staff member is not required to use other equipment to communicate about their workflow. Limiting the equipment helps to reduce the risk of infection transmission within the hospital.

Attention is now directed to embodiments which may be best understood by reference to the figures. The following description is intended only by way of example, and simply illustrates certain example embodiments. It should be noted that various figures include a reference numeral within a circle; these notations are only for ease of distinguishing certain features in the drawings and do not actually appear on the interface when viewed by a user.

Referring to FIG. 1, a system 100 in an embodiment is shown. Network 130 operative connects a number of components, including Mobile Device 110 and Transport Management System 120. An example of a Transport Management System 140 is TransportTracking from TeleTracking Technologies, Inc., of Pittsburgh, Pa. Mobile Device 110 preferably has a touch sensitive display, which is sometime called a "touch screen" for convenience, and may also be known as or called a touch-sensitive display system.

Figure 2:
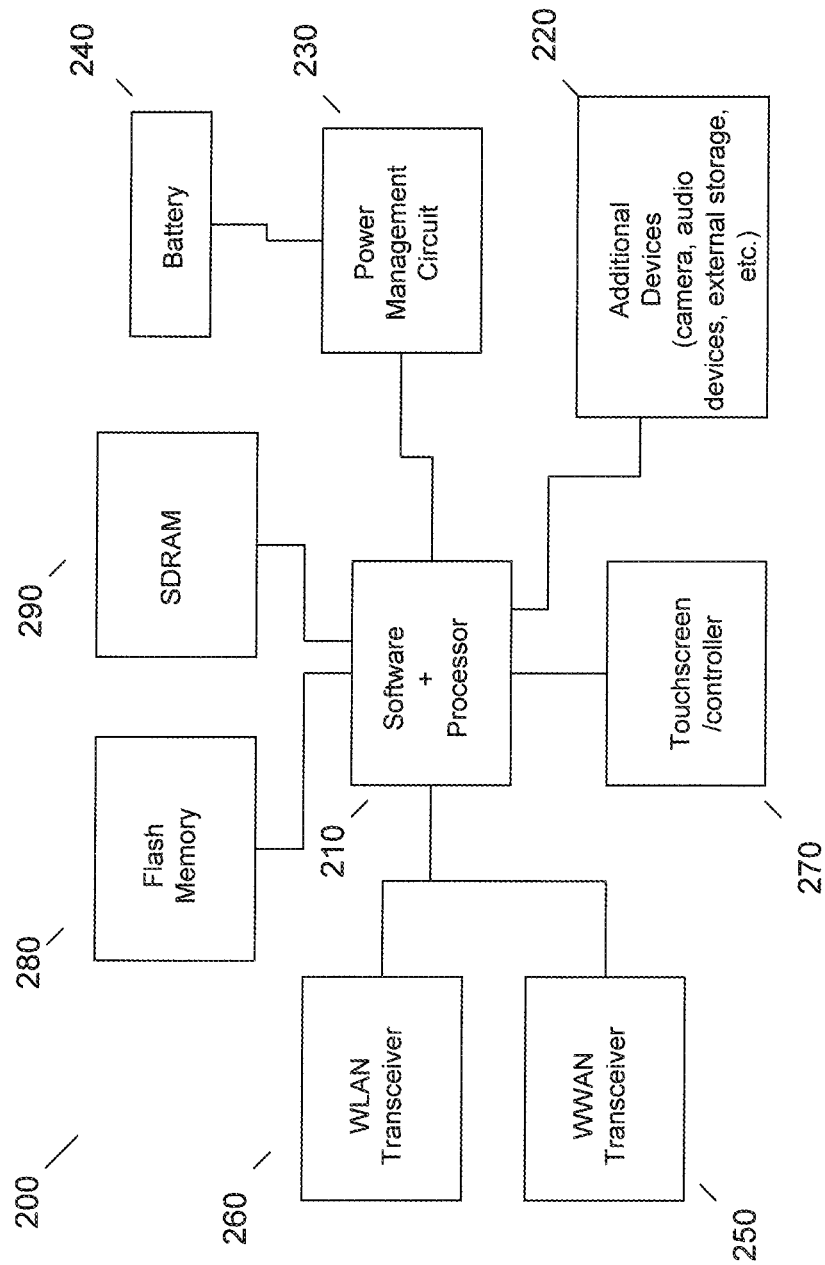
FIG. 2 illustrates an example mobile information handling device and components thereof.

Referring now to FIG. 2, with regard to mobile device circuitry 200, an example includes an ARM based system (system on a chip) design, with software and processor(s) combined in a single chip 210. Internal busses and the like depend on different vendors, but essentially all the peripheral devices (220) may attach to a single chip 210. In contrast to the circuitry illustrated in FIG. 1, the tablet circuitry 200 combines the processor, memory control, and I/O controller hub all into a single chip 210. Also, ARM based systems 200 do not typically use SATA or PCI or LPC. Common interfaces for example include SDIO and I2C. There are power management chip(s) 230, which manage power as supplied for example via a rechargeable battery 240, which may be recharged by a connection to a power source (not shown), and in the at least one design, a single chip, such as 210, is used to supply BIOS like functionality and DRAM memory.

ARM based systems 200 typically include one or more of a WWAN transceiver 250 and a WLAN transceiver 260 for connecting to various networks, such as telecommunications networks and wireless base stations. Commonly, an ARM based system 200 will include a touchscreen 270 for data input and display. In a touch-sensitive device, a touch-sensitive screen provides an input interface and an output interface between the device and a user. ARM based systems 200 also typically include various memory devices, for example flash memory 280 and SDRAM 290.

Figure 3:
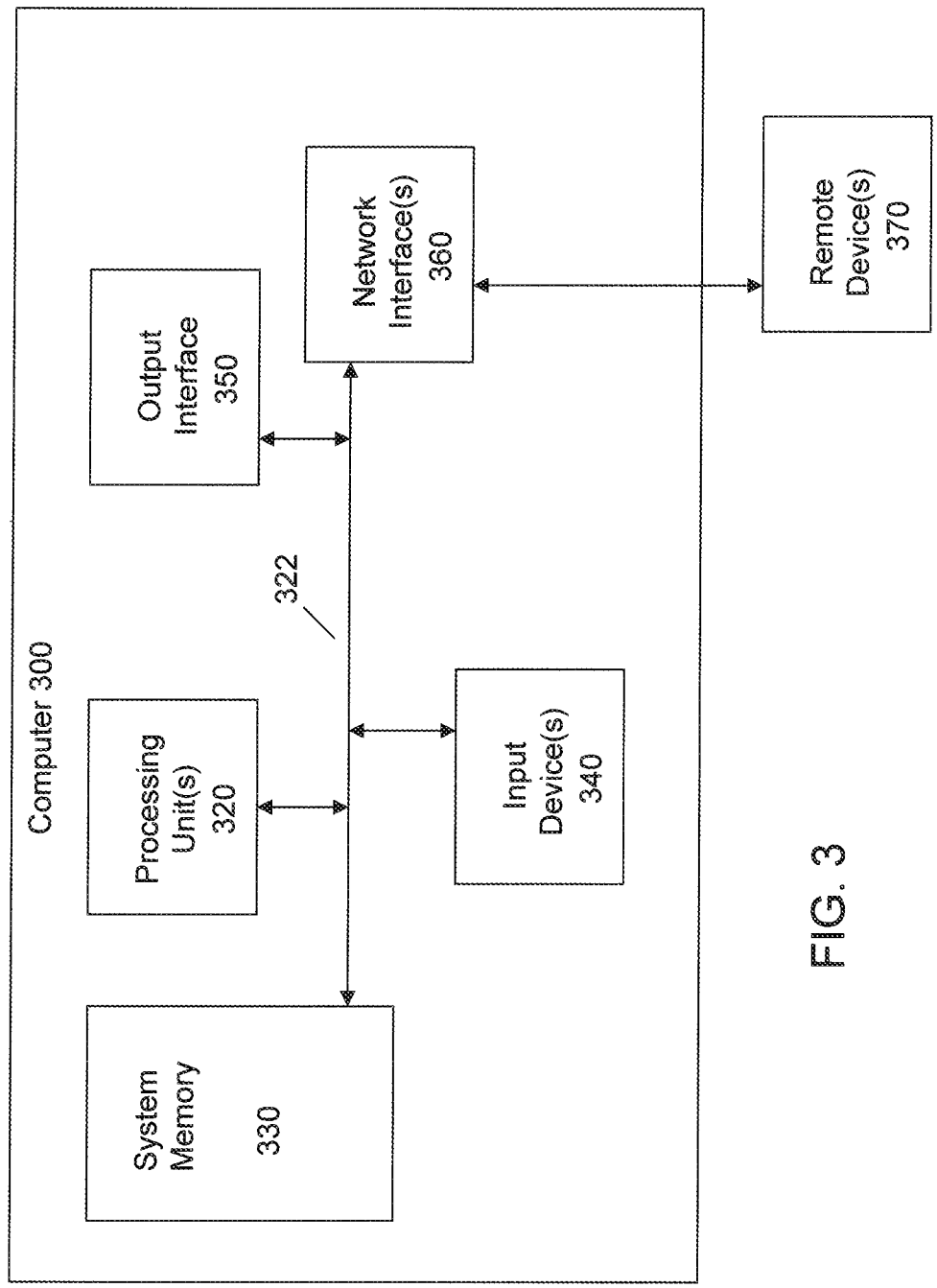
FIG. 3 illustrates an example information handling device and components thereof.

ARM based systems 200 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document Referring now to FIG. 3, an example device that may be used in implementing one or more embodiments, such as a server in the Transport Management System, includes a computing device in the form of an information handling device 300. This example device may be a server used in one of the systems in hospital network, or one of the portable electronic devices connected to the hospital network. Components of information handling device 300 may include, but are not limited to, a processing unit 320, a system memory 330, and a system bus 322 that couples various system components including the system memory 330 to the processing unit 320. Information handling device 300 may include or have access to a variety of computer readable media, including databases (not shown). The system memory 330 may include non-signal computer readable storage media, for example in the form of volatile and/or nonvolatile memory such as read only memory (ROM) and/or random access memory (RAM). By way of example, and not limitation, system memory 330 may also include an operating system, application programs, other program modules, and program data.

A user can interface with (for example, enter commands and information) the information handling device 300 through input devices 340. A display or other type of device can also be connected to the system bus 322 via an interface, such as an output interface 350. In addition to a display, information handling devices may also include other peripheral output devices. The information handling device 300 may operate in a networked or distributed environment using logical connections to one or more other remote device(s) 370 such as other computers. The logical connections may include network interface(s) 360 to a network, such as a local area network (LAN), a wide area network (WAN), and/or a global computer network, but may also include other networks/buses.

Figure 4:
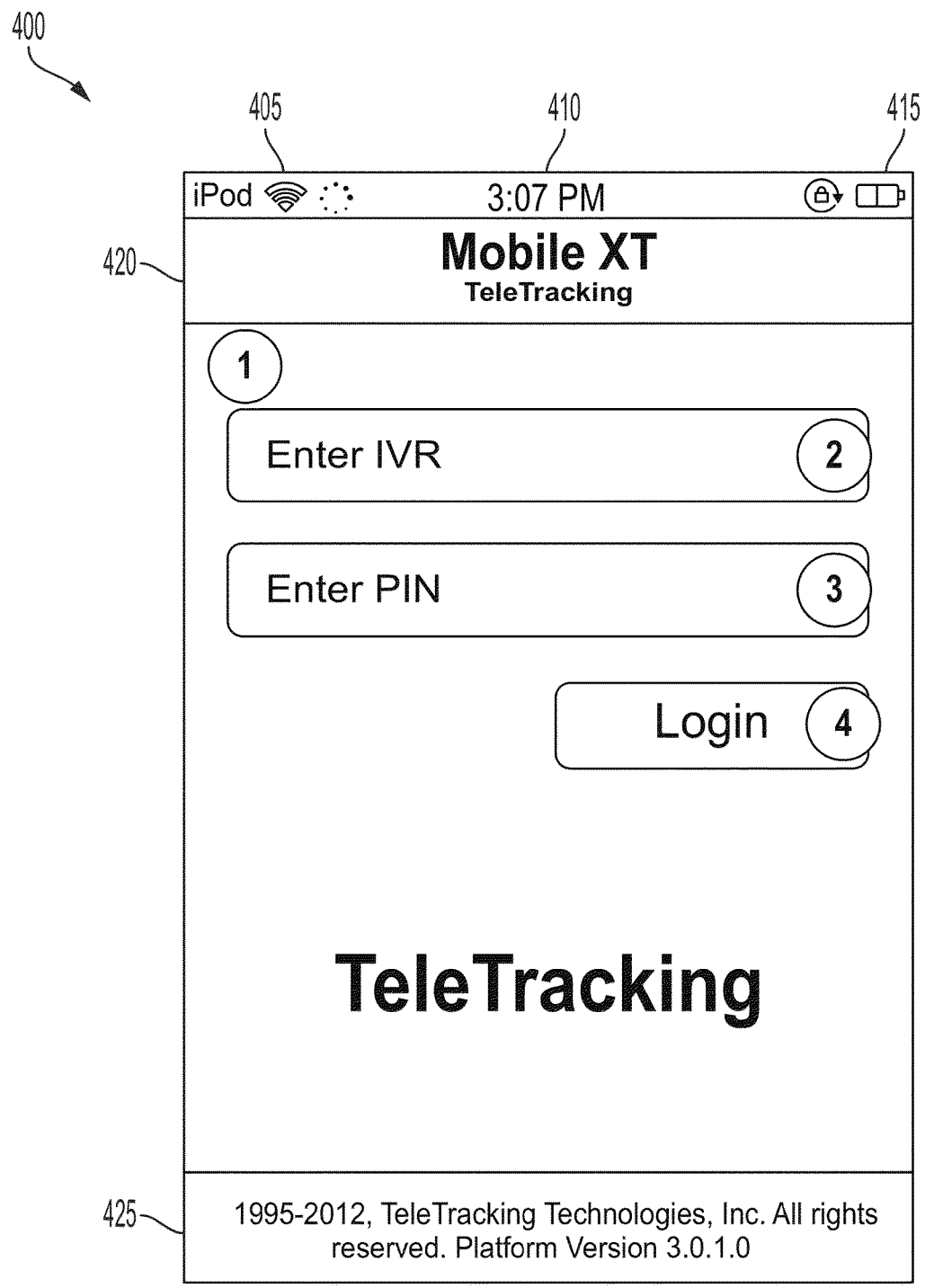
FIG. 4 illustrates an exemplary user interface for a user to login to a Transport Management system.

FIG. 4 illustrates an exemplary user interface for a user to login to Transport Management System 120. In some embodiments, user interface 400 includes the following elements or a subset or superset thereof: signal strength indicator(s) 405 for wireless communication(s), such as cellular and Wi-Fi signals; time 410; battery status indicator 415; vertical area 420 which, as shown, displays the name of the application running on the mobile computing device; and vertical area 460, in which legal notices may be placed (e.g., copyright notices, etc.). Certain elements, such as 405, 410, and 415 may be provided by the device operating system.

The user is not required to log in every time the devices is used to complete and action. Once logged in, a user will remain logged in unless a pre-determined timeout period expires or a user does a log out for the day. Figure reference 1 identifies a section of the user interface that may be used for displaying massages based on user actions (no message is shown). For example, when a user does an action that redirects to the login page, a message may show for a predetermined time period (preferably about 10 seconds) describing the action that was just performed. Figure reference 2 identifies a textbox where the user may input the user's login name. Figure reference 3 identifies a text box where a user may input their Personal Identification Number (i.e., password). Figure reference 4 identifies a button, which is enabled once a user has entered the required criteria, and upon touch authenticates the user and logs the user into the Transport Management System, which on successful authentication, associates the current device to the logged in user.

Figure 5:
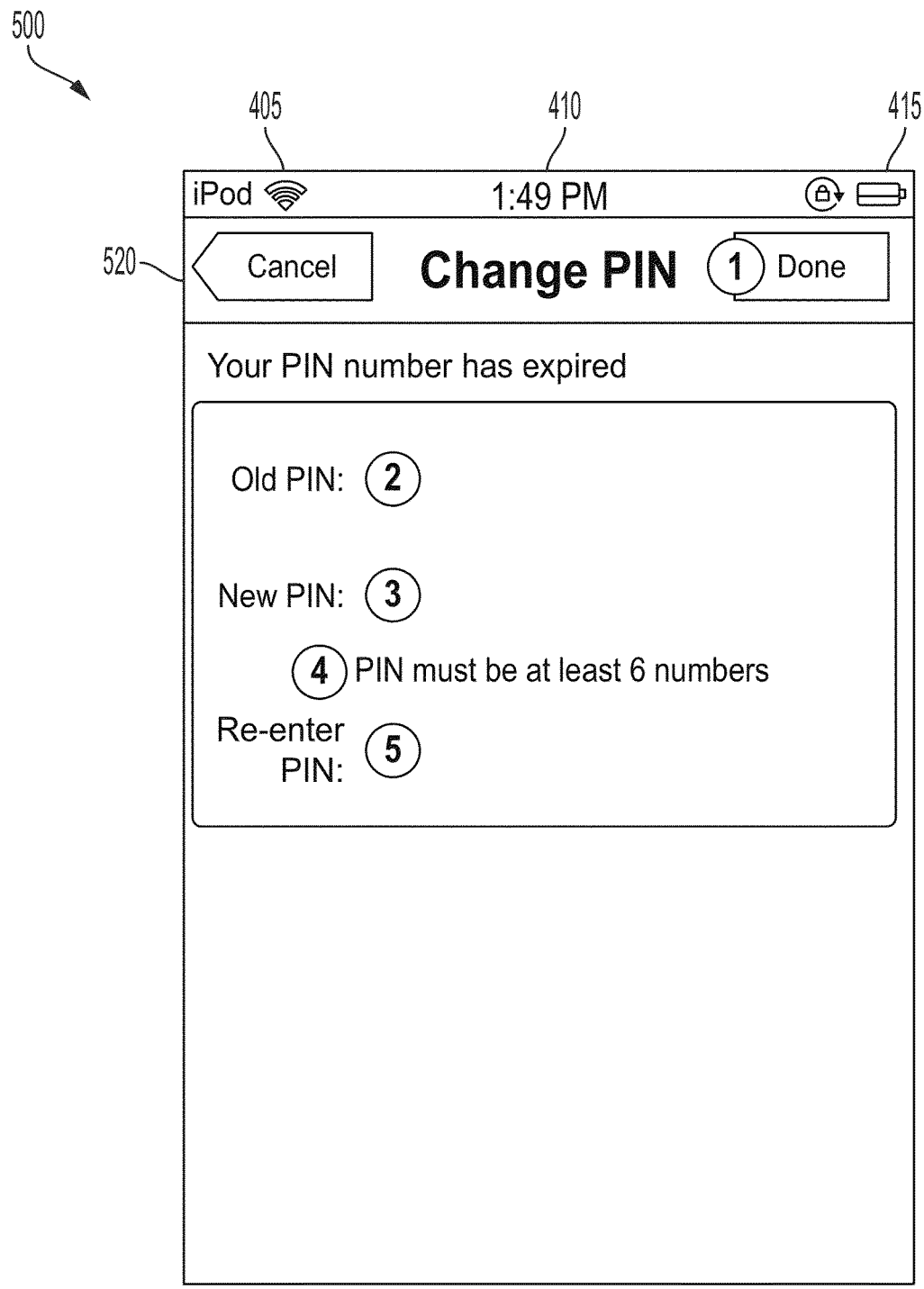
FIG. 5 illustrates an exemplary user interface for changing a user's pin upon expiration in accordance with some embodiments.

FIG. 5 illustrates an exemplary user interface to a Transport Management System for changing a user's pin upon expiration in accordance with some embodiments. In some embodiments, user interface 500 includes the following elements, or a subset or superset thereof: 405, 410, 415, a described above; and vertical area 520, which contains a user interface label and two indications of where a user may press to either cancel or complete the operation. Figure reference 1 identifies a button, enabled when a user has entered the required criteria, and upon touch validates that the new PIN meets the hospital's requirements and saves. Figure reference 2 identifies a text box where a user enters their previous (i.e., current) PIN. Figure reference 3 identifies a textbox where a user enters their new PIN. Figure reference 4 identifies a label which displays a message identifying the hospital's minimum character limitation for PINs. Figure reference 5 identifies a textbox where a user may re-enter their new PIN.

Figure 5A:
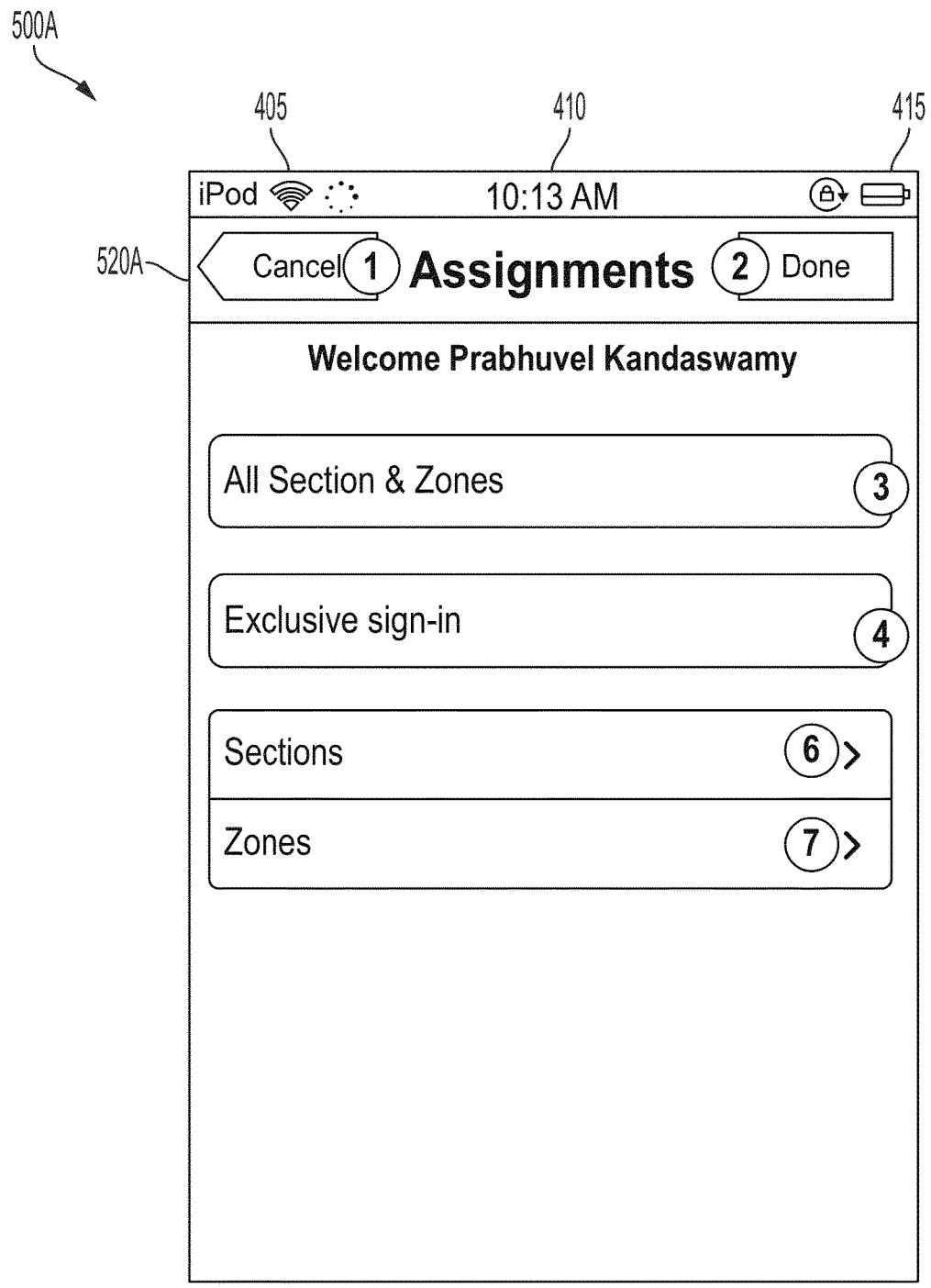
FIG. 5a illustrates an exemplary user interface for an employee to enter into a Transport Management System the employee's work areas in some embodiments.

FIG. 5a illustrates an exemplary user interface for setting work areas in some embodiments. In some embodiments, user interface 500A includes the following elements, or a subset or superset thereof: 405, 410, 415, a described above; and vertical area 520, which contains a user interface label and two indications of where a user may press to either cancel or complete the operation. Figure reference 1 indicates a button and when touched will show an alert asking for confirmation of the request to cancel. Figure reference 2 indicates a button that is enables once the user has selected a valid assignment. Upon touch, the selected assignment is saved and navigation is to the home page. Figure reference 3 indicates a button that is activated by touch and selects all sections and zones as the user's assignment. Figure reference 4 indicates a button which is touch activated and upon being selected makes the transporter the exclusive transporter for the selected assignment. Figure reference 6 indicates a button which is touch activated and upon selection will navigate to the sections screen (500B). Figure reference 7 indicates a button which is touch activated and upon selection will navigate to the zones screen (500C).

Figure 5B:
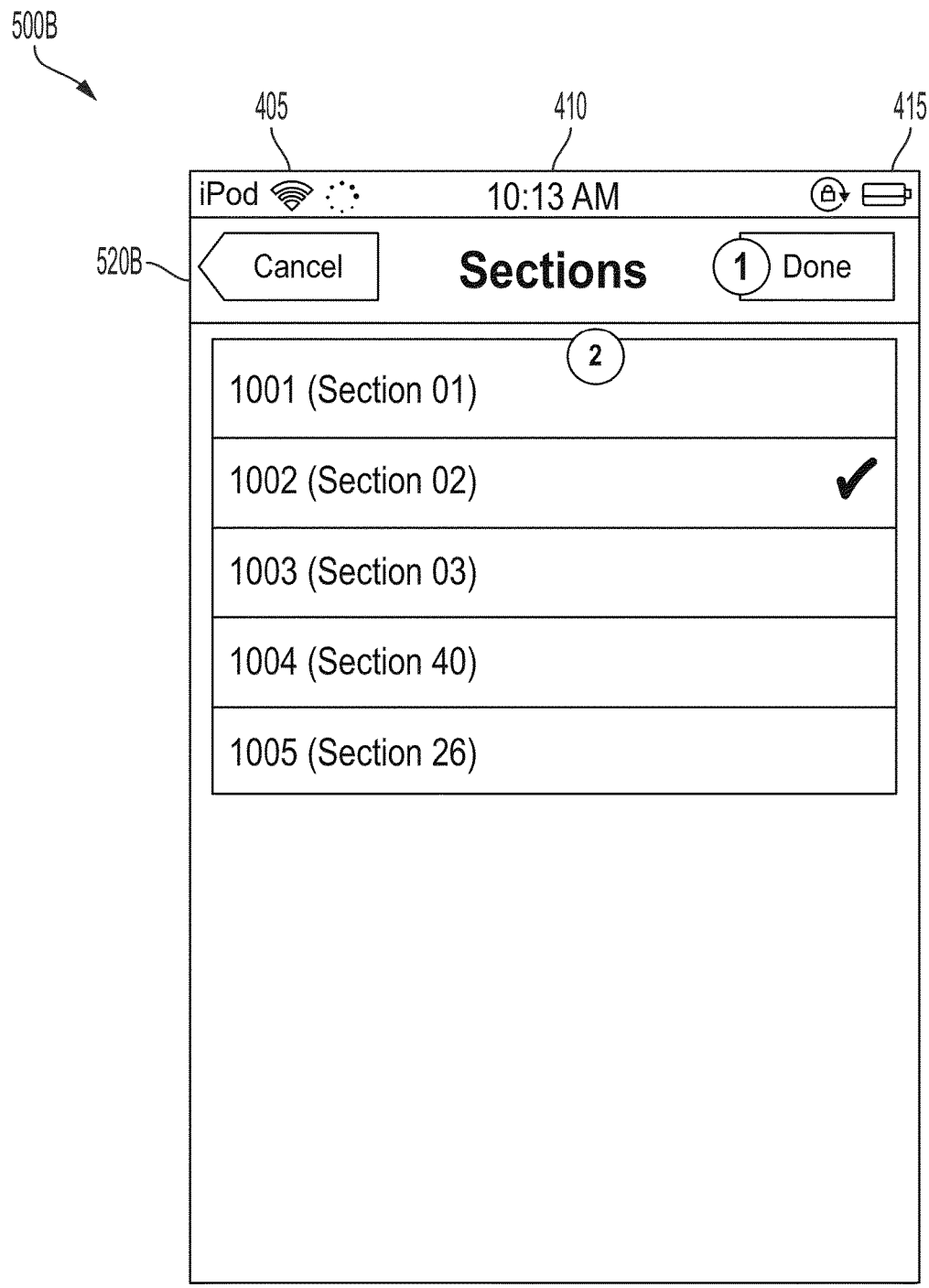
FIG. 5b illustrates an exemplary user interface for an employee to enter into a Transport Management System the employee's work areas in some embodiments.

FIG. 5B illustrates an exemplary user interface for setting work areas in some embodiments. In some embodiments, user interface 500B includes the following elements, or a subset or superset thereof: 405, 410, 415, a described above; and vertical area 520B, which contains a user interface label and two indications of where a user may press to either cancel or complete the operation. Figure reference 1 indicates a button selected by touch and upon selection will save the selected sections and return to the assignment screen. Reference FIG. 2 indicates a list which displays all sections. The user may touch a displayed section to add that section to their assignment. A checkmark will appear to indicate selection. More than one section may be selected. All zones within a section will be selected or de-selected when the section is selected or de-selected.

Figure 5C:
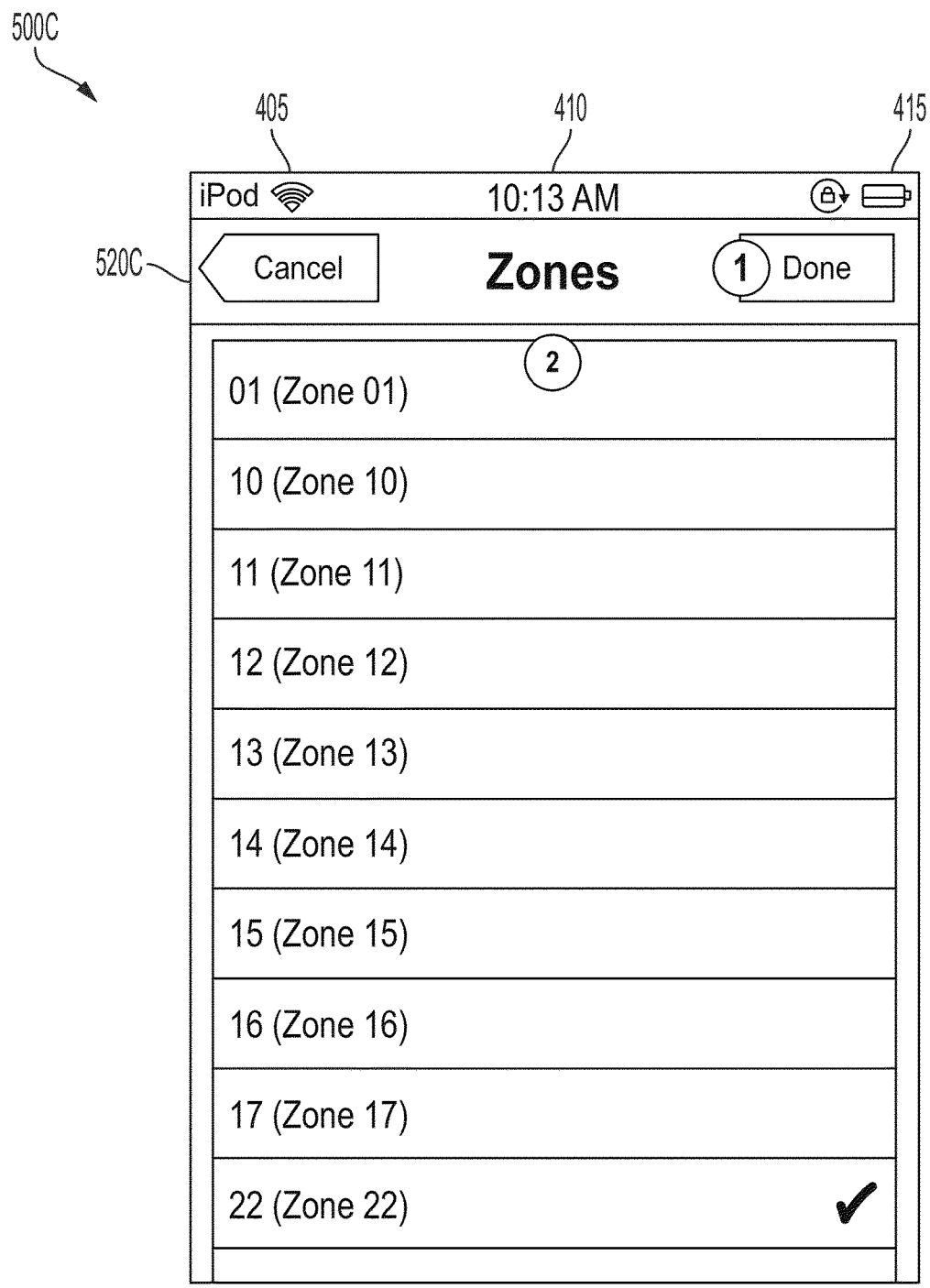
FIG. 5c illustrates an exemplary user interface for viewing an employee to enter into a Transport Management System the employee's work areas in some embodiments.

FIG. 5C illustrates an exemplary user interface for setting work areas in some embodiments. In some embodiments, user interface 500C includes the following elements, or a subset or superset thereof: 405, 410, 415, a described above; and vertical area 520C, which contains a user interface label and two indications of where a user may press to either cancel or complete the operation. Figure reference 1 indicates a button activated by touch which upon selection saves selected zones and returns to the assignment screen. Figure reference 2 indicates a list which displays all zones. The user may touch a displayed zone to add that zone to their assignment. A checkmark will appear to indicate selection. More than one zone may be selected. If a zone has been selected as a result of a user selecting a section, those zones will already be associated with a checkmark and will be disable from being unselected in this screen.

Figure 6:
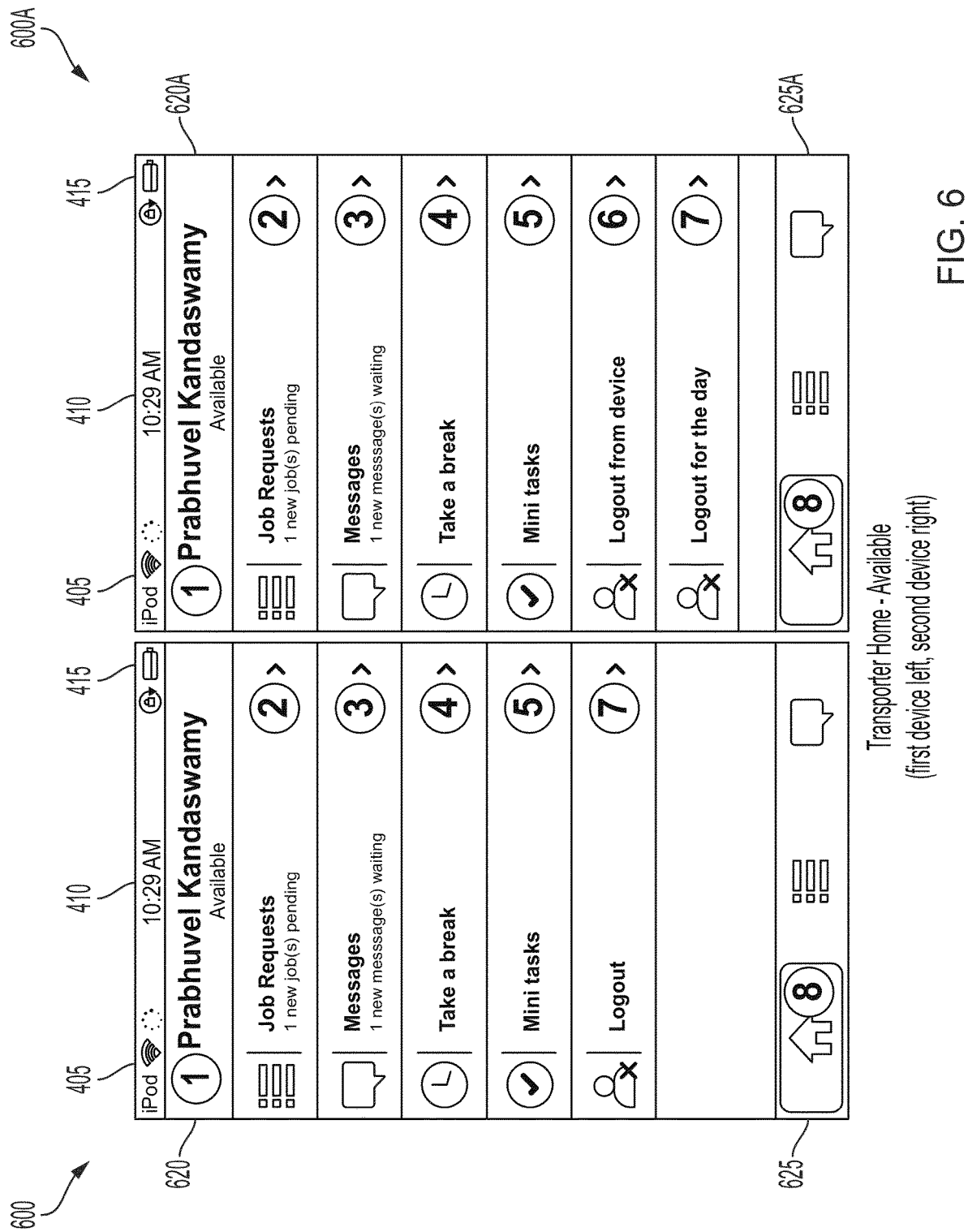
FIG. 6 illustrates an exemplary user interface displaying the current status of a transporter and other available actions in some embodiments.

FIG. 6 illustrates an exemplary user interface displaying the current status of a transporter and other available actions in some embodiments. In some embodiments, user interface 600 includes the following elements, or a subset or superset thereof: 405, 410, 415, a described above; vertical area 620, which contains a user interface label (Available) and two indications of where a user may press to either cancel or complete the operation; and vertical area 625 which provides short cuts to some of the more frequently accessed tasks (home, joblist, and messages). Figure reference 1 indicates a label which shows three different pieces of information: the first line shows the name of the logged in user; the second line shows the user's current status; and the third line displays confirmation messages based on actions the user has performed. Figure reference 2 indicates a button which is activated by touch. If the user is currently dispatched or in progress with a job, navigation is to the job details of that job. Otherwise if the user has self-dispatch permission, navigation is to the job list screen. Otherwise, a user is presented with job details of an available job. This is disabled when a user is on break. If there are pending jobs, an indication of how many jobs are pending is shown. Figure reference 3 indicates a button selected by touch and which navigates to the messages screen. If a user has new messages, the number of new messages will be displayed; this is not displayed once the user has visited the messages screen. Figure reference 4 indicates a button selected by touch and which navigates to a take a break screen. This is disabled when a user is not in available status and when a user is on break, this becomes return to work. Figure reference 5 indicates a button selected by touch and which navigates to the mini task screen. This is disabled when a user is not in available status. Figure reference 7 indicates a button activated by touch and which logs out a user. This button is enabled only when a user is in available status. Figure reference 8 indicates an icon. When the user is at the home screen, this navigational button will be highlighted and the touch action will be disabled. In some embodiments, user interface 600A includes the same elements as user interface 600, with the addition of Figure reference 6, which permits a user to logout from the specific device, but not for the day.

Figure 7:
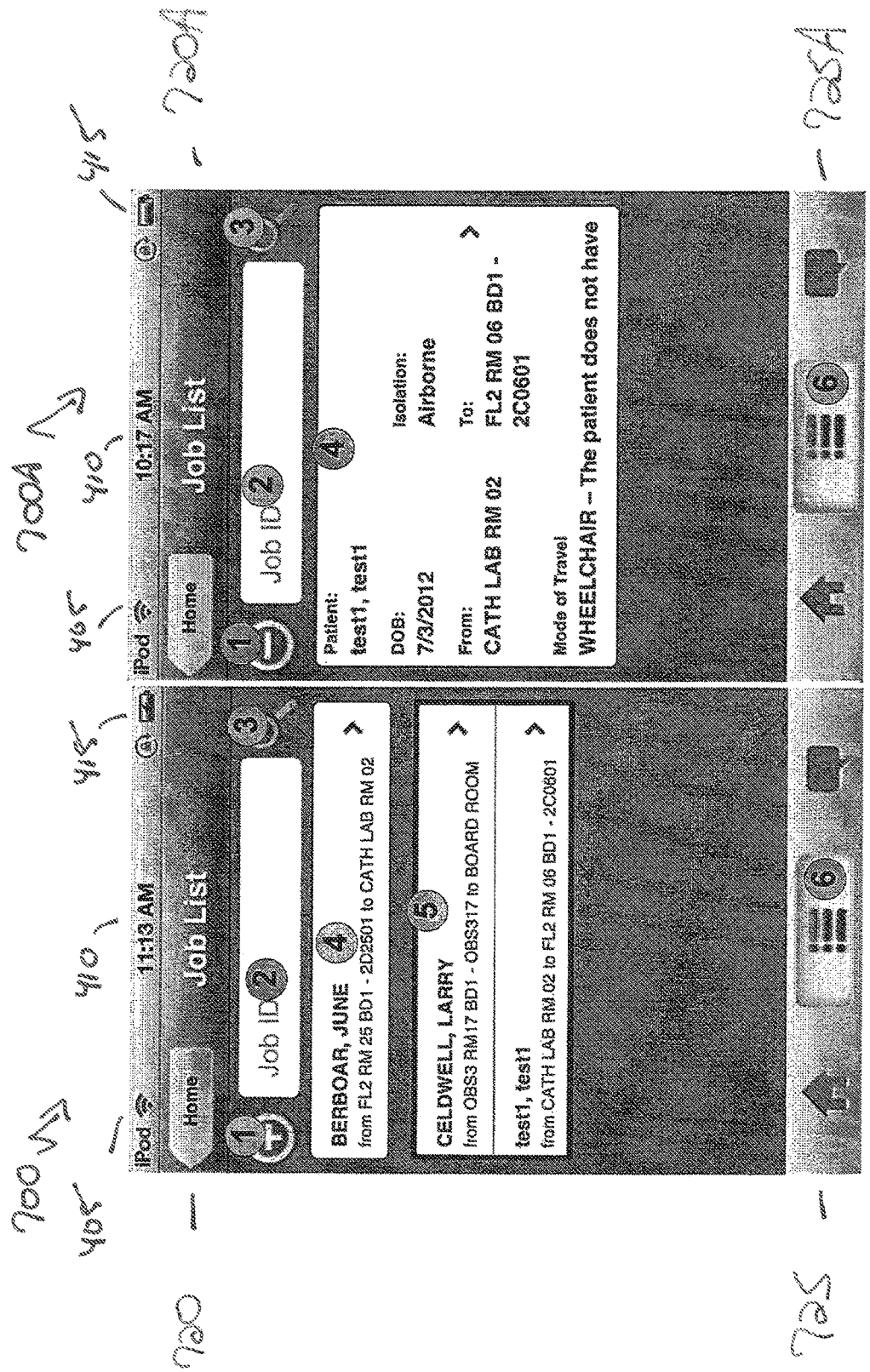
FIG. 7 illustrates an exemplary user interface by which a transporter may search for and start a new job in some embodiments.

FIG. 7 illustrates an exemplary user interface to a Transport Management System by which a transporter may search for and start a new job in some embodiments. In some embodiments, user interface 700 (used by a supervisor with self-dispatch authority, shown in a collapsed view) includes the following elements, or a subset or superset thereof: 405, 410, 415, as described above; vertical area 720, which contains a user interface label and an indication of where a user may press to return home; and vertical area 725 which provides short cuts to some of the more frequently accessed tasks (home, joblist, and messages). Figure reference 1 indicates a button (+), when touched by a user, will expand the list of available jobs to show full job details for all jobs. Figure reference 2 identifies a search box where a user may enter a job identifier to search for a job. Figure reference 3 identifies a button, enabled when a user has entered a value into the textbox at Figure reference 2, and upon touch searches for a job with the identifier that matches the value entered at Figure reference 2. Figure reference 4 is a label/link which displays a job (with truncated details) the system has automatically assigned to the user. Figure reference 5 is a list, only displayed if the logged in user is has supervisor authority, and shows a lists of all jobs that are pending in the transporter's campus (i.e., facility). Figure reference 6 is a joblist quick navigation icon, which is highlighted to show the user is at the joblist.

In some embodiments, user interface 700A (used by a transporter with self-authority, shown in an expanded view) includes the following elements, or a subset or superset thereof: 405, 410, 415, as described above; vertical area 720, which contains a user interface label and an indication of where a user may press to return home; and vertical area 725A which provides short cuts to some of the more frequently accessed tasks (home, joblist, and messages). Figure reference 1 indicates a button (−), when touched by a user, will collapse the list of available jobs to show truncated job details for all jobs. Figure reference 2 identifies a search box where a user may enter a job identifier to search for a job. Figure reference 3 identifies a button, enabled when a user has entered a value into the textbox at Figure reference 2, and upon touch searches for a job with the identifier that matches the value entered at Figure reference 2. Figure reference 4 is a label/link which displays a job (with full details) the system has automatically assigned to the user. Figure reference 6 is a joblist quick navigation icon, which is highlighted to show the user is at the joblist.

Figure 8:
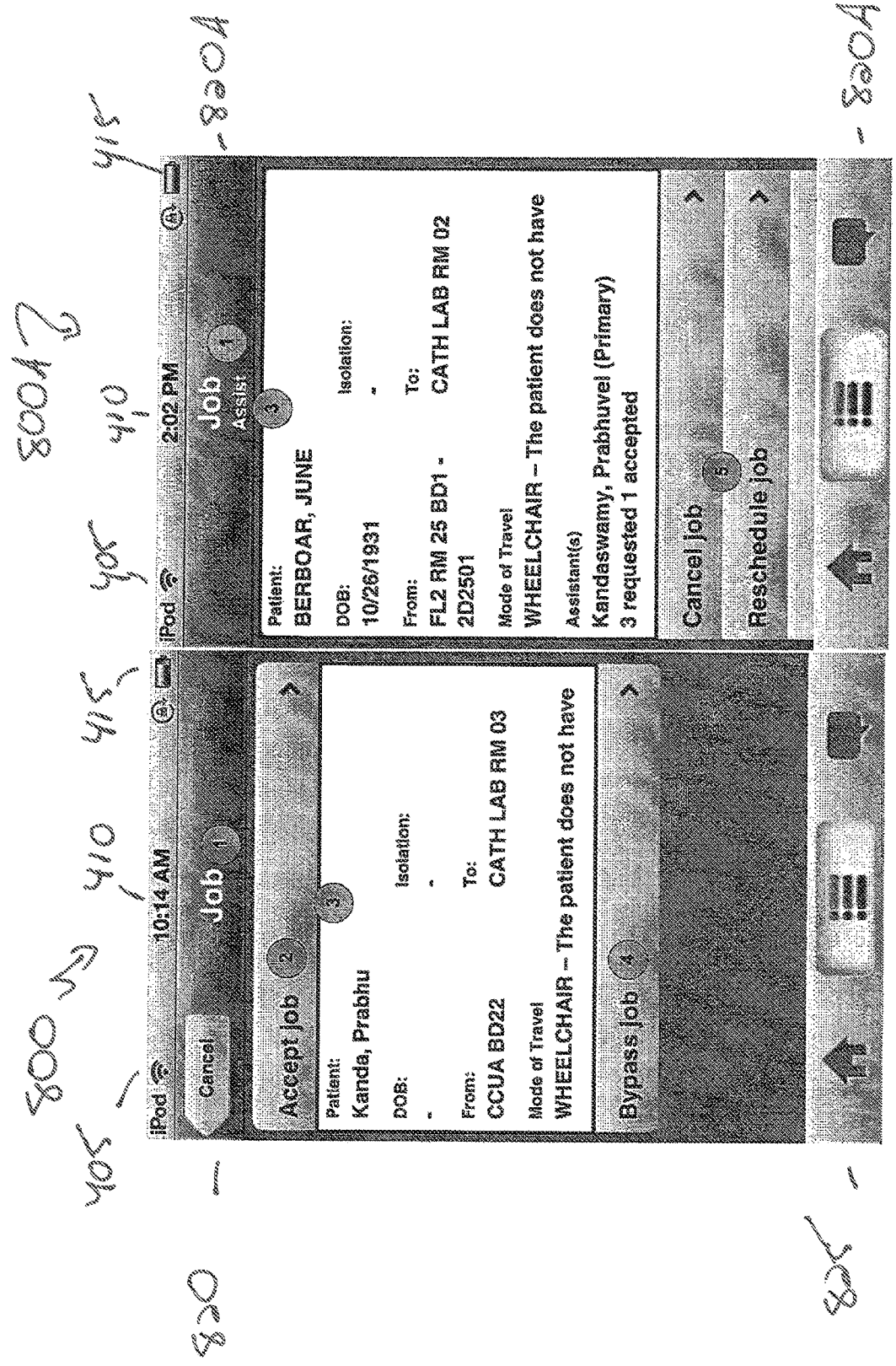
FIG. 8 illustrates an exemplary user interface which presents the job details of a transport job and the available actions for the transporter in some embodiments.

FIG. 8 illustrates an exemplary user interface to a Transport Management System which presents the job details of a transport job and the available actions for the transporter in some embodiments. In some embodiments, user interface 800 (showing job details for a regular transport job) includes the following elements, or a subset or superset thereof: 405, 410, 415, a described above; vertical area 820, which contains a user interface label and an indication of where a user may press to cancel the operation; and vertical area 825 which provides short cuts to some of the more frequently accessed tasks (home, joblist, and messages). Figure reference 1 indicates a message area and if a user is redirected to this screen by performing an action, a message describing that action is displayed until the user navigates to another page. Figure reference 2 indicates a button that indicates job status action and upon touch navigates to the job status screen (not displayed on an assist job). Figure reference 3 is a label showing job details for the selected job (no data is shown by "-"). For a patient transport job the following information, or sub-set thereof, may be shown: Patient Name, Date of Birth, Reason Code, Isolation, Origin, Designation, Mode of Travel, Travel Requirements, and a Media Player if special instructions have been recorded for the job. Other information may also be shown. For an item transport job the following information, or sub-set thereof, may be shown: Item Name, Patient Name, Reason Code, Isolation, Origin, Destination, Mode of Travel, Travel Requirements, and a Media Player if special instructions have been recorded for the job. For an outpatient transport job the following information, or sub-set thereof, may be shown: Reason Code, Isolation, Origin, Destination, Mode of Travel, and a Media Player if special instructions have been recorded for the job. Figure reference 4 identifies a button, available when the transporter status is available and visible if the logged-in user has permission to bypass jobs, and upon touch will bypass the presented job. Upon bypass, processing and retrieving new job screens will be displayed, after which the user will be presented with a new job. This section may also display a button for each permission based action the user may perform (i.e., Request assistance, round Trip, Delay, Resume, Reschedule, Cancel, Request Assistance, and Release Self).

In some embodiments, user interface 800A (showing job details for an transport assist job) includes the following elements, or a subset or superset thereof: 405, 410, 415, a described above; vertical area 820A, which contains a user interface label and an indication of where a user may press to cancel the operation; and vertical area 825A which provides short cuts to some of the more frequently accessed tasks (home, joblist, and messages). Figure reference 1 indicates a message area and if a user is redirected to this screen by performing an action, a message describing that action is displayed until the user navigates to another page. Figure reference 3 is a label showing job details for the selected job (no data is shown by "-"). For a patient transport job the following information, or sub-set thereof, may be shown: Patient Name, Date of Birth, Reason Code, Isolation, Origin, Designation, Mode of Travel, Travel Requirements, and a Media Player if special instructions have been recorded for the job. For an item transport job the following information, or sub-set thereof, may be shown: Item Name, Patient Name, Reason Code, Isolation, Origin, Destination, Mode of Travel, Travel Requirements, and a Media Player if special instructions have been recorded for the job. For an outpatient transport job the following information, or sub-set thereof, may be shown: Reason Code, Isolation, Origin, Destination, Mode of Travel, and a Media Player if special instructions have been recorded for the job. Figure reference 5 identifies buttons, available when the transporter status is available and visible if the logged-in user has permission to perform the actions indicated, to cancel the job and to reschedule the job. This section may also display a button for each permission based action the user may perform (i.e., Request assistance, round Trip, Delay, Resume, Reschedule, Cancel, Request Assistance, and Release Self).

Figure 9:
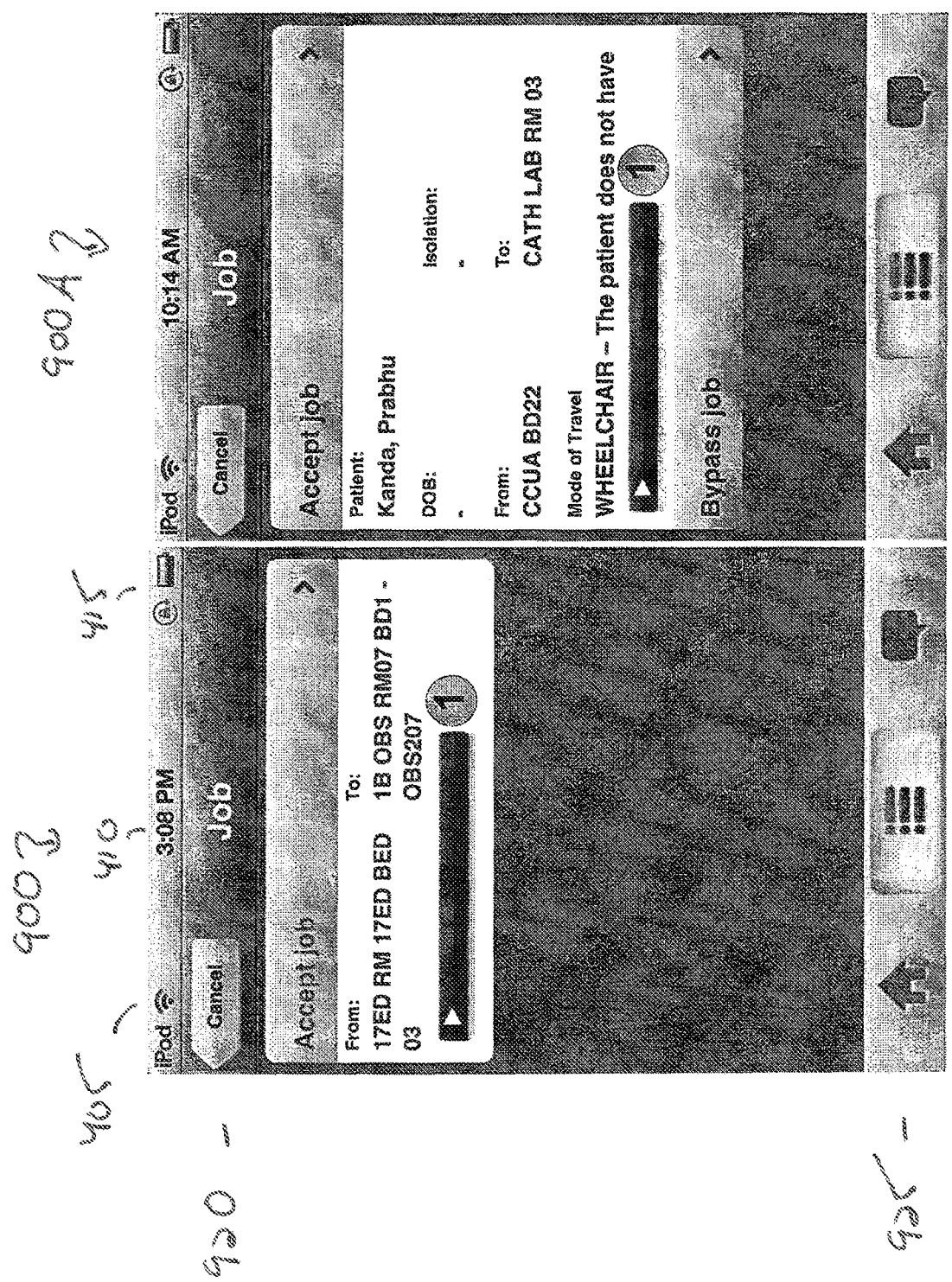
FIG. 9 illustrates an exemplary user interface for viewing special instructions that are recorded as a voice message in some embodiments.

FIG. 9 illustrates an exemplary user interface to a Transport Management System for viewing special instructions that are recorded as a voice message in some embodiments. In some embodiments, user interface 900 includes the following elements, or a subset or superset thereof: 405, 410, 415, a described above; vertical area 920 which contains a user interface label and an indication of where a user may press to cancel the operation; and vertical area 925A which provides short cuts to some of the more frequently accessed tasks (home, joblist, and messages). Figure reference 1 identifies a media player, which when selected, will play a recorded voice message. Once the voice message is played, the user interface will be updated (900A) to display job details and available actions (i.e., accept job and bypass job).

Figure 10:
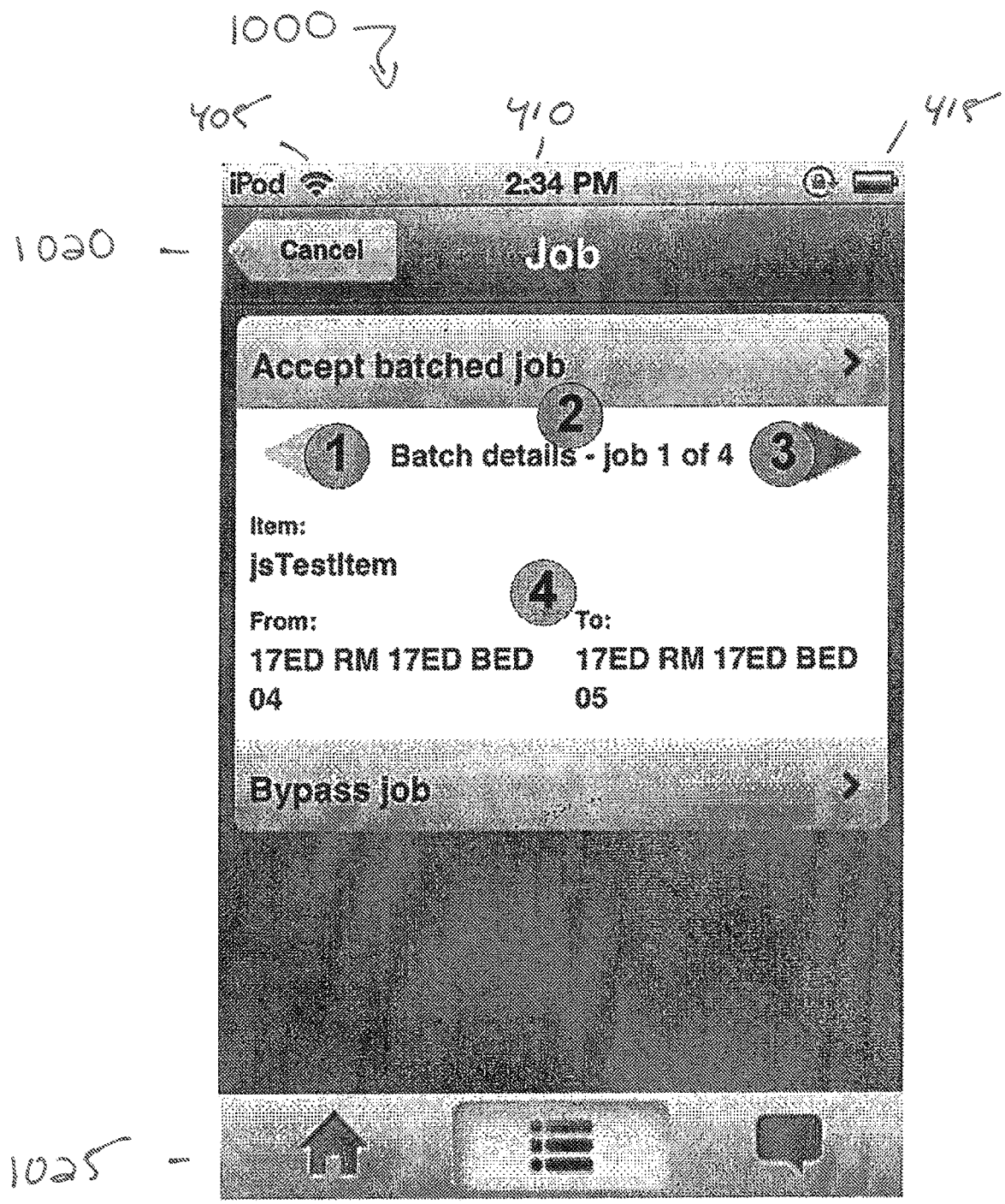
FIG. 10 illustrates an exemplary user interface for viewing details of a job in some embodiments.

FIG. 10 illustrates an exemplary user interface to a Transport Management System for viewing details of a job in some embodiments. In some embodiments, user interface 1000 (showing details of a batch item job) includes the following elements, or a subset or superset thereof: 405, 410, 415, a described above; and vertical area 1020, which contains a user interface label and an indication of where a user may press to cancel the operation. Figure reference 1 indicates a button which when touched, shows details of the previous job in the batch. Figure reference 2 indicates a label showing, as part of the title, the current index of the job details being viewed and the total jobs in the batch. Figure reference 3 indicates a button which when touched shows details of the next job in the batch. Figure reference 4 indicates the item job details. Permission based user actions (i.e., accept batched job and bypass job) are also shown.

Figure 11:
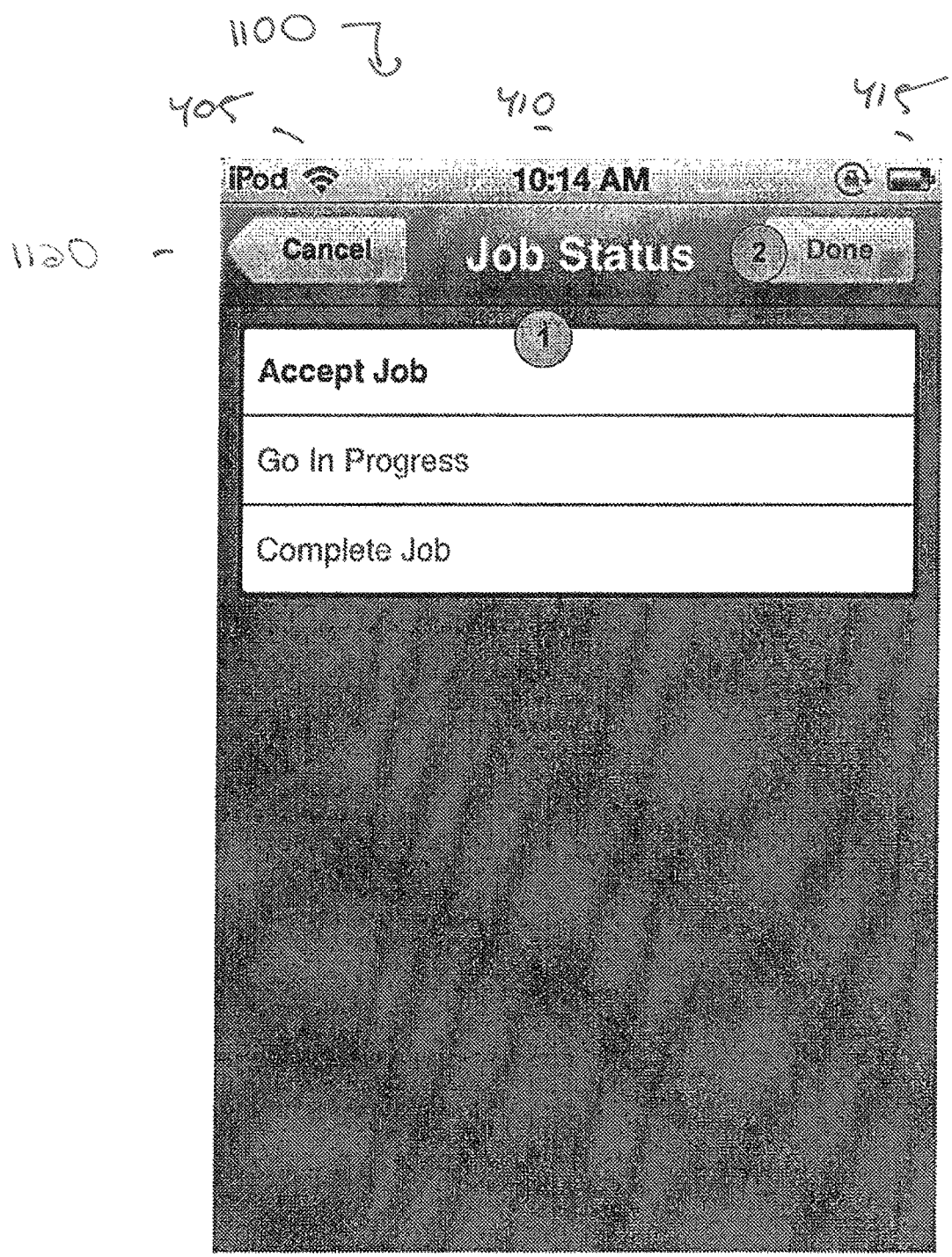
FIG. 11 illustrates an exemplary user interface for viewing a list of actions which advance the job status in some embodiments.

FIG. 11 illustrates an exemplary user interface to a Transport Management System for viewing a list of actions which advance the job status in some embodiments In some embodiments, user interface 1100 includes the following elements, or a subset or superset thereof: 405, 410, 415, a described above; and vertical area 1120, which contains a user interface label and an indication of where a user may press to cancel the operation. Figure reference 1 indicates a list of action which advance the job status. One action is enabled at a time, based on the logged-in transporter's status; the other two are disabled. If the transporter is Available, "Accept Job" will be enabled (shown); if the transporter is Dispatched, "Go In Progress" will be enabled; if the transporter is in Progress, "Complete Job" will be enabled. A checkmark will appear near the item that has been selected. Figure reference 2 indicates a button which is enabled once the user has selected the available action, and upon touch will show the processing screen and perform the selected action.

Figure 12:
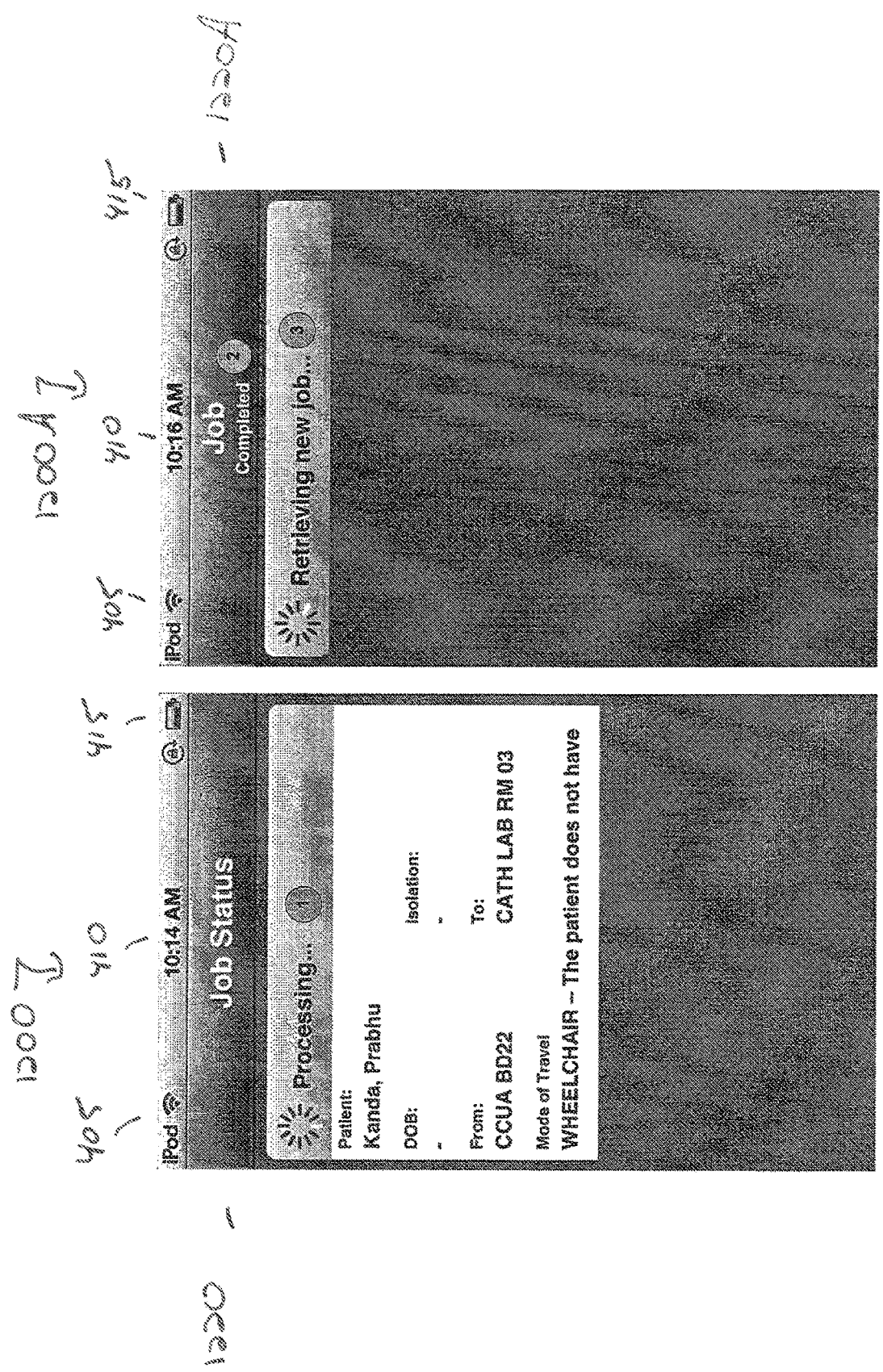
FIG. 12 illustrates an exemplary user interface for showing a user that an action has been performed in some embodiments.

FIG. 12 illustrates an exemplary user interface to a Transport Management System for showing a user that an action has been performed in some embodiments. In some embodiments, user interface 1200 (showing processing of job) includes the following elements, or a subset or superset thereof: 405, 410, 415, a described above; and vertical area 1220, which contains a label. Figure reference 1 indicates a processing label which shows a user that they have performed an action. If the user has just put a job in process, the processing screen will navigate to the Bed Details of that job with the next available action. If there is an error while processing the action, an alert will be displayed and the user returned to the previous screen so the user may attempt the action again.

In some embodiments, user interface 1200A (showing retrieving of new job) includes the following elements, or a subset or superset thereof: 405, 410, 415, a described above; and vertical area 1220, which contains a label. Figure reference 2 appears on user interface 1200A. If a user is redirected to this screen by performing an action, a message describing that action will be displayed until the user navigates to another page. Figure reference 3 indicate a label showing the user that they are about to be presented with a new job. If there are no pending jobs, an alert indicating such will be displayed and the user returned to the home screen.

Figure 13:
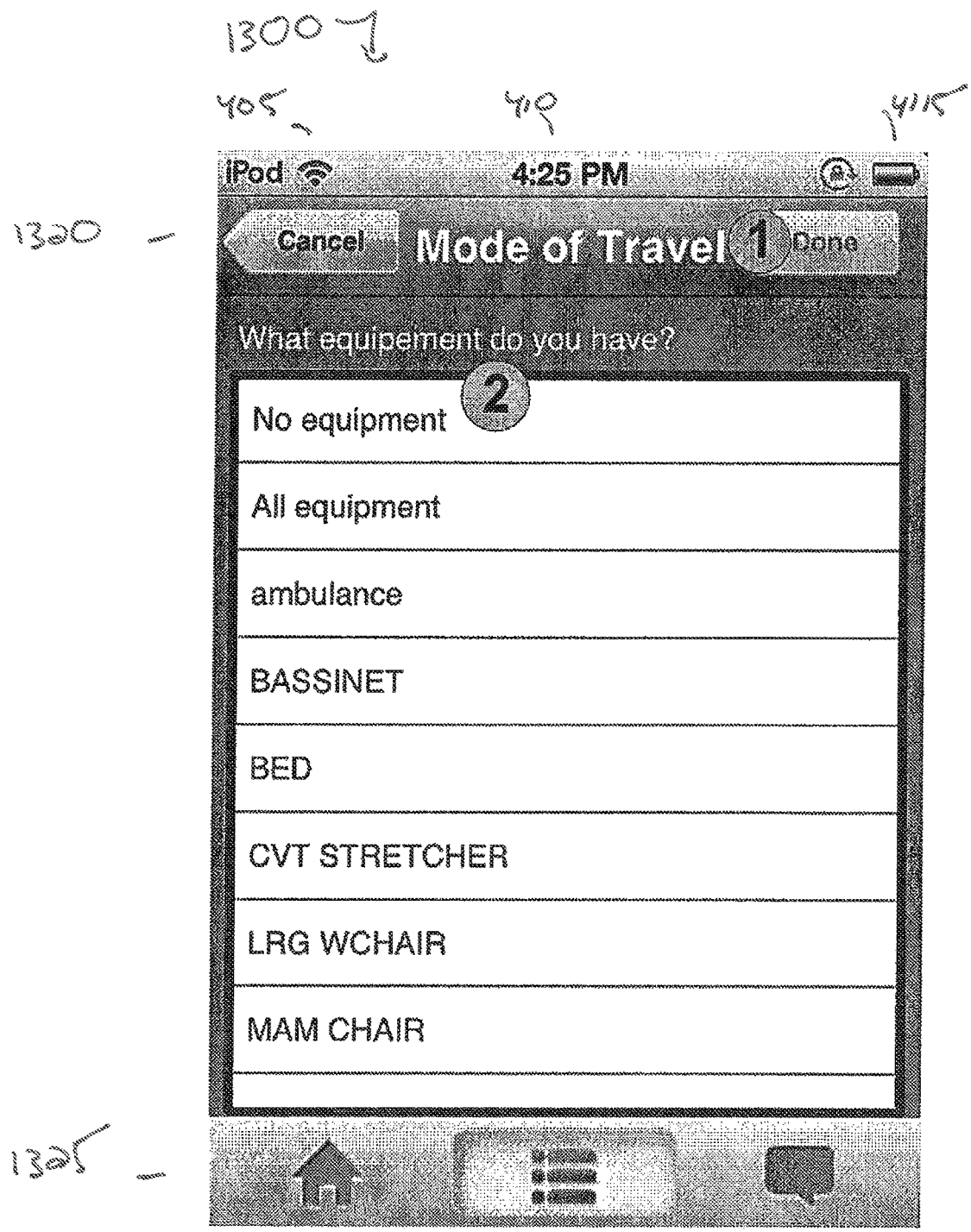
FIG. 13 illustrates an exemplary user interface for selecting mode of travel before a transporter picks up a job in some embodiments.

FIG. 13 illustrates an exemplary user interface to a Transport Management System for selecting mode of travel before a transporter picks up a job in some embodiments. In some embodiments, user interface 1300 (showing mode of travel) includes the following elements, or a subset or superset thereof: 405, 410, 415, a described above; vertical area 1320, which contains a user interface label (Mode of Travel) and two indications of where a user may press to either cancel or complete the operation; and vertical area 1325 which provides short cuts to some of the more frequently accessed tasks and, as shown, indicates the task being viewed (Joblist). Figure reference 1 indicates a button, only enabled if a user has selected a mode of travel, and upon touch selects the mode of travel and presents a transporter with a job. Figure reference 2 indicates a list of mode of travel for the hospital's campus (i.e., facility); a user may touch a row to select it. A check mark will appear near the selected mode to indicate selection.

Figure 14:
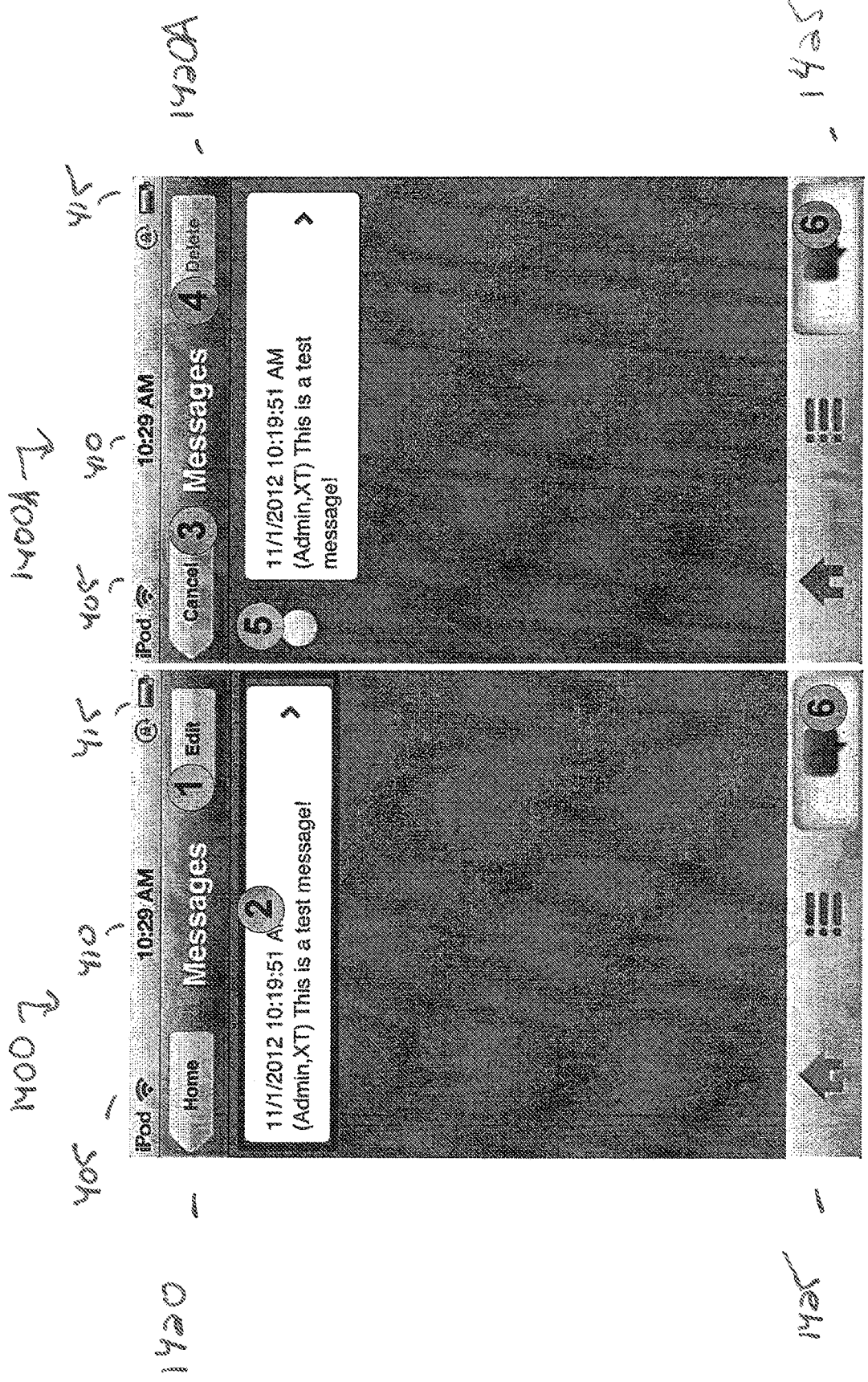
FIG. 14 illustrates an exemplary user interface for viewing messages sent to the user after logging in for the day.

FIG. 14 illustrates an exemplary user interface to a Transport Management System for viewing messages sent to the user after logging in for the day. In some embodiments, user interface 1400 (showing normal messages) includes the following elements, or a subset or superset thereof: 405, 410, 415, a described above; vertical area 1420, which contains a label identifying the screen being displayed (Messages) and two indications of where a user may press to either return home or edit a message; and vertical area 1425 which provides short cuts to some of the more frequently accessed tasks and, as shown, indicates the task being viewed (Messages). Figure reference 1 indicates a button, which is only visible if a user has one or more messages, and upon touch enables deleting of notifications. Figure reference 2 indicates a list which shows all instant notifications the user has received since logging in. Figure reference 6 is a message quick navigation icon, which is highlighted to show the user is at messages.

In some embodiments, user interface 1400A (showing message edit mode) includes the following elements, or a subset or superset thereof: 405, 410, 415, a described above; vertical area 1420A, which contains a label identifying the screen being displayed (Messages) and two indications of where a user may press to either return home or edit a message; and vertical area 1425A which provides short cuts to some of the more frequently accessed tasks and, as shown, indicates the task being viewed (Messages). User interface 1400A is obtained by pressing the edit button in user interface 1400. In this user interface (1400A) a checkbox appears next to the notifications that may be deleted and the edit button of user interface 1400 is replaced with a cancel button in this user interface (1400A), which disables notification deleting. Figure reference 3 indicates a button which upon touch exists edit mode. Figure reference 4 indicates a button which upon touch deletes any checked messages. Figure reference 5 indicates a checkbox for selecting messages to be deleted; if checked the message is marked for deletion and upon touch, if unchecked, it is set to checked and if checked, it is set to unchecked. Figure reference 6 is a message quick navigation icon, which is highlighted to show the user is at messages.

FIG. 15 illustrates an exemplary user interface to a Transport Management System for viewing a message sent to the user through Transport Management System 120 in some embodiments. In some embodiments, user interface 1500 (showing edit mode) includes the following elements, or a subset or superset thereof: 405, 410, 415, a described above; vertical area 1520, which contains a message label and two indications of where a user may press to either return home or re-order the message; and vertical area 1525, which provides a short cuts to delete the message. Figure reference 7 indicates a button containing an up arrow and a down arrow, and upon touch either moves the message above or below the currently displayed message. Figure reference 8 indicates the full text of the message being viewed. Figure reference 9 indicates a button for deleting the message being viewed. Upon touch an alert is displayed seeking confirmation of the deletion with yes and no buttons. If confirmation is forthcoming, the message is deleted and the next newest message (the message above the deleted one) is displayed. If there is no newer message, navigation is back to the full list.

Figure 16:
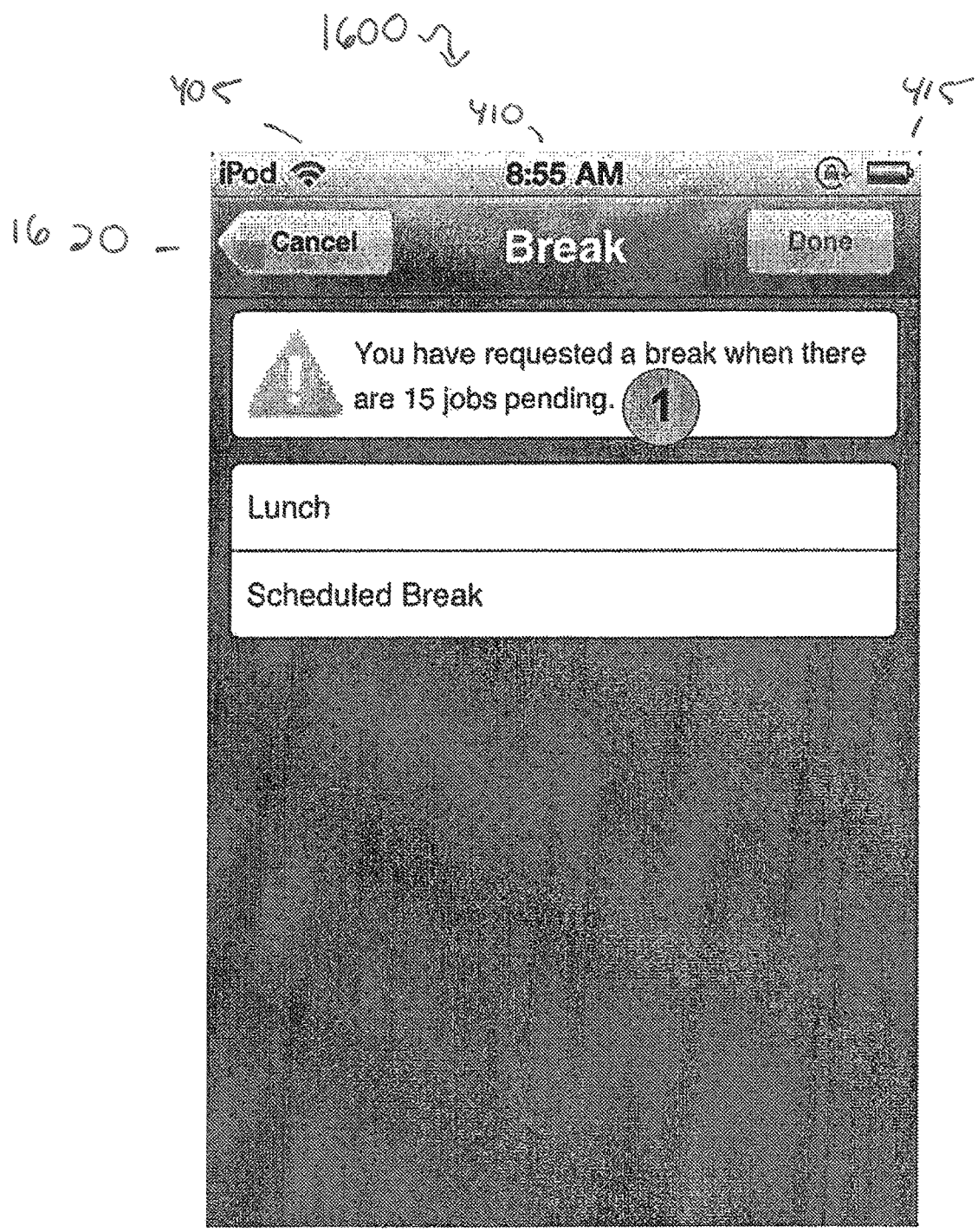
FIG. 16 illustrates an exemplary user interface for a transporter to indicate they will be taking a lunch break or a scheduled break in some embodiments.

FIG. 16 illustrates an exemplary user interface to a Transport Management System for a transporter to indicate they will be taking a lunch break or a scheduled break in some embodiments. In some embodiments, user interface 1600 (for transporter break) includes the following elements, or a subset or superset thereof: 405, 410, 415, a described above; and vertical area 1620, which contains a label identifying the screen being displayed (Break) and two indications of where a user may press to either return cancel or signal completion. Figure reference 1 indicates a label which may display a warning in certain circumstances, i.e., when the number of pending jobs exceeds a pre-determined level. Various types of approved breaks are displayed for a user to select.

Figure 17:
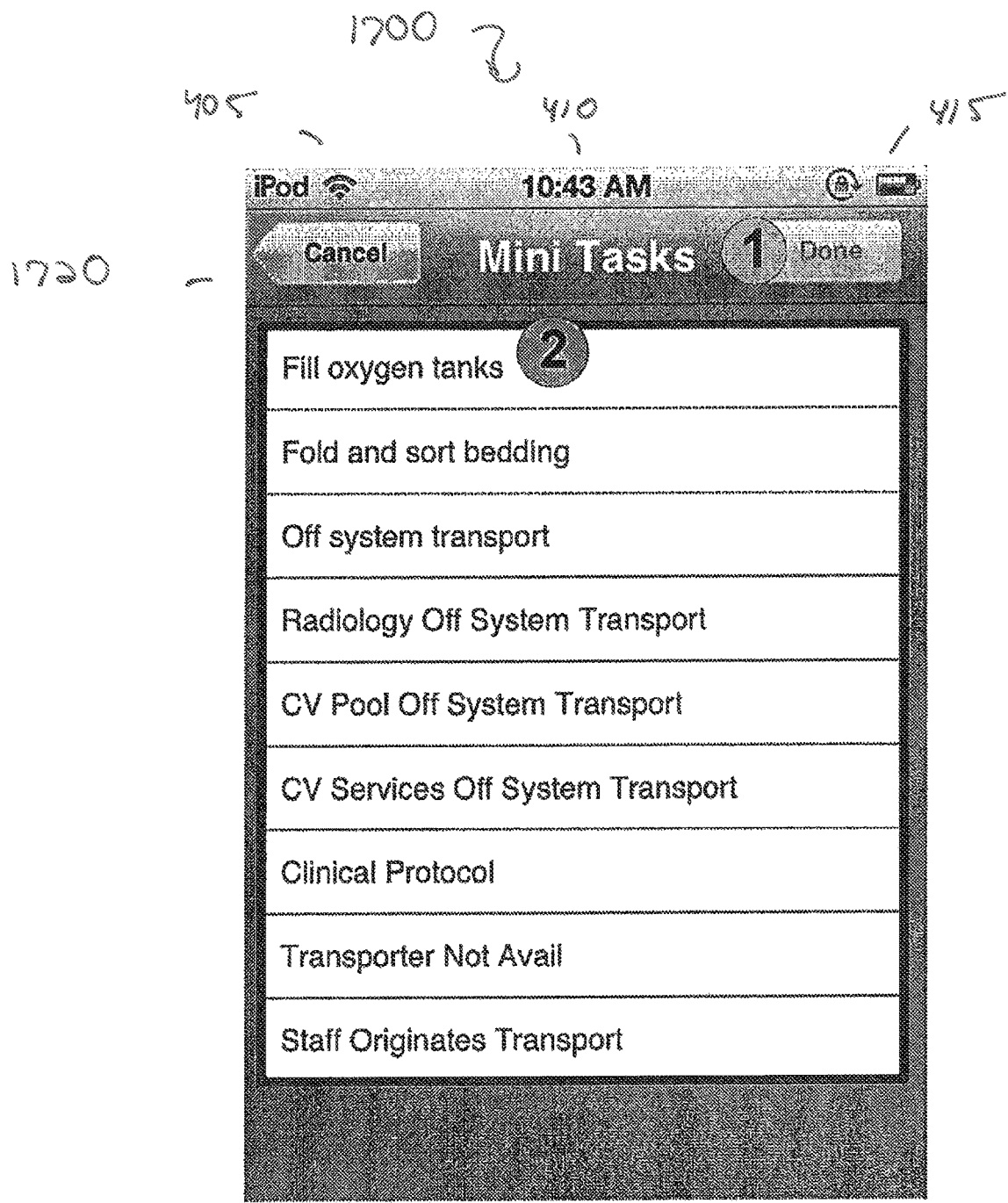
FIG. 17 illustrates an exemplary user interface for a transporter to record mini tasks completed in some embodiments.

FIG. 17 illustrates an exemplary user interface to a Transport Management System for a transporter to record mini tasks completed in some embodiments. In some embodiments, user interface 1700 (for showing recording of mini task) includes the following elements, or a subset or superset thereof: 405, 410, 415, a described above; vertical area 1720, which contains a label identifying the screen being displayed (Mini Tasks) and an indications of where a user may press to cancel and return to the previous screen and to complete interaction with this screen. Figure reference 1 indicates a button which, upon touch, records the selected mini task for the logged-in user and returns to the home screen. Figure reference 2 indicates a list of pre-determined mini tasks at the hospital facility. A user may touch a row to select the mini task therein and a checkmark will appear to indicate the selection. A user may only select one mini task at a time.

Figure 18:
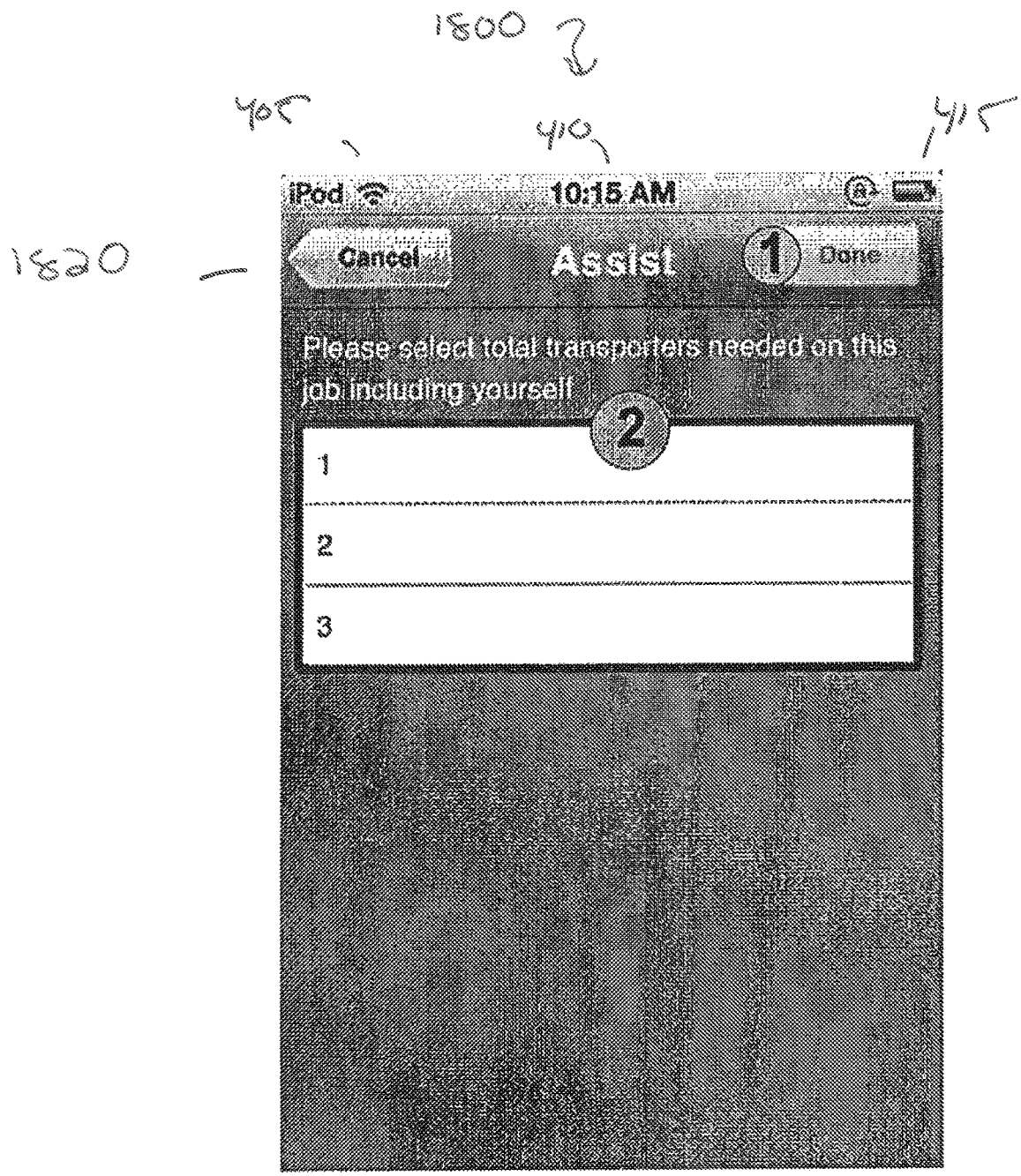
FIG. 18 illustrates an exemplary user interface by which a transporter may set the number of transporters required to carry out the current job in some embodiments.

FIG. 18 illustrates an exemplary user interface to a Transport Management System by which a transporter may set the number of transporters required to carry out the current job in some embodiments. In some embodiments, user interface 1800 (for Assist) includes the following elements, or a subset or superset thereof: 405, 410, 415, as described above; and vertical area 1820, which contains a label identifying the screen being displayed (Assist) and indications of where a user may press to cancel and return to the previous message screen or conclude with the current screen. Figure reference 1 indicates a button which, upon touch, saves the number of transporters needed for the current job to the Transport Management System 120 and navigates back to the job details screen. Figure reference 2 indicates a list of the number of transporters required, which may vary from 1 to the pre-determined maximum number of transporters per job. A checkmark will appear to indicate the selected number. The transporter must select the total number of transporters, including him/herself.

Figure 19:
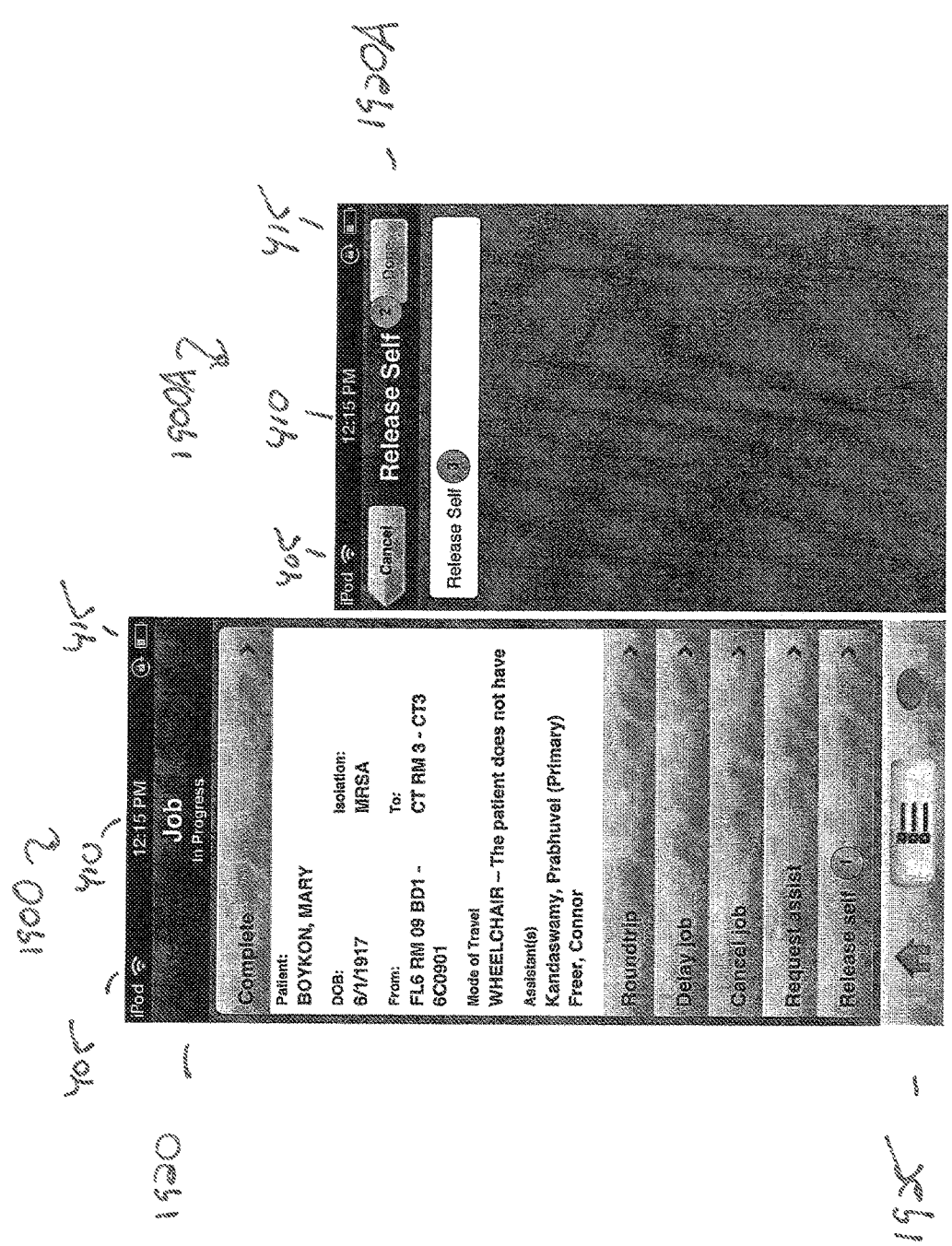
FIG. 19 illustrates an exemplary user interface by which a transporter may remove his/her self from a job after having requested assistance.

FIG. 19 illustrates an exemplary user interface to a Transport Management System by which a transporter may release him/herself from the job after requesting assistance. In some embodiments, user interface 1900 includes the following elements, or a subset or superset thereof: 405, 410, 415, as described above; vertical area 1920, which contains a label identifying the screen being displayed (Job in Progress); and vertical area 1925 which provides short cuts to some of the more frequently accessed tasks and, as shown, indicates the task being viewed (Joblist). Details of the job are displayed together with various options for the job (i.e., complete, roundtrip, delay job, cancel job, request assist, and release self). Figure reference 1 indicates a button which is only available to a primary transporter who is in progress with a assist job (meaning that all required assistants have joined). Upon touch, the user is navigated to the resume job screen (1900A).

In some embodiments, user interface 1900A includes the following elements, or a subset or superset thereof: 405, 410, 415, as described above; vertical area 1920A, which contains a label identifying the screen being displayed (Release Self) and user indications for canceling and returning to the prior screen or indicating interaction with this screen is complete. Figure reference 2 indicates a button which is only enabled if the user has selected "release self" below. Upon touch, the logged-in user is removed from the current job, status is changed to available, and the user is presented with a new job. The first assistant who was dispatched will become the new primary transporter and that job's number of required transporters is reduced by one. The processing and retrieving new job screens are preferred to be shown after the button is touched. If there are no available jobs, navigation will be to the home screen. Figure reference 3 indicates a button which, upon touch, will be selected and a checkmark will appear once selected.

Figure 20:
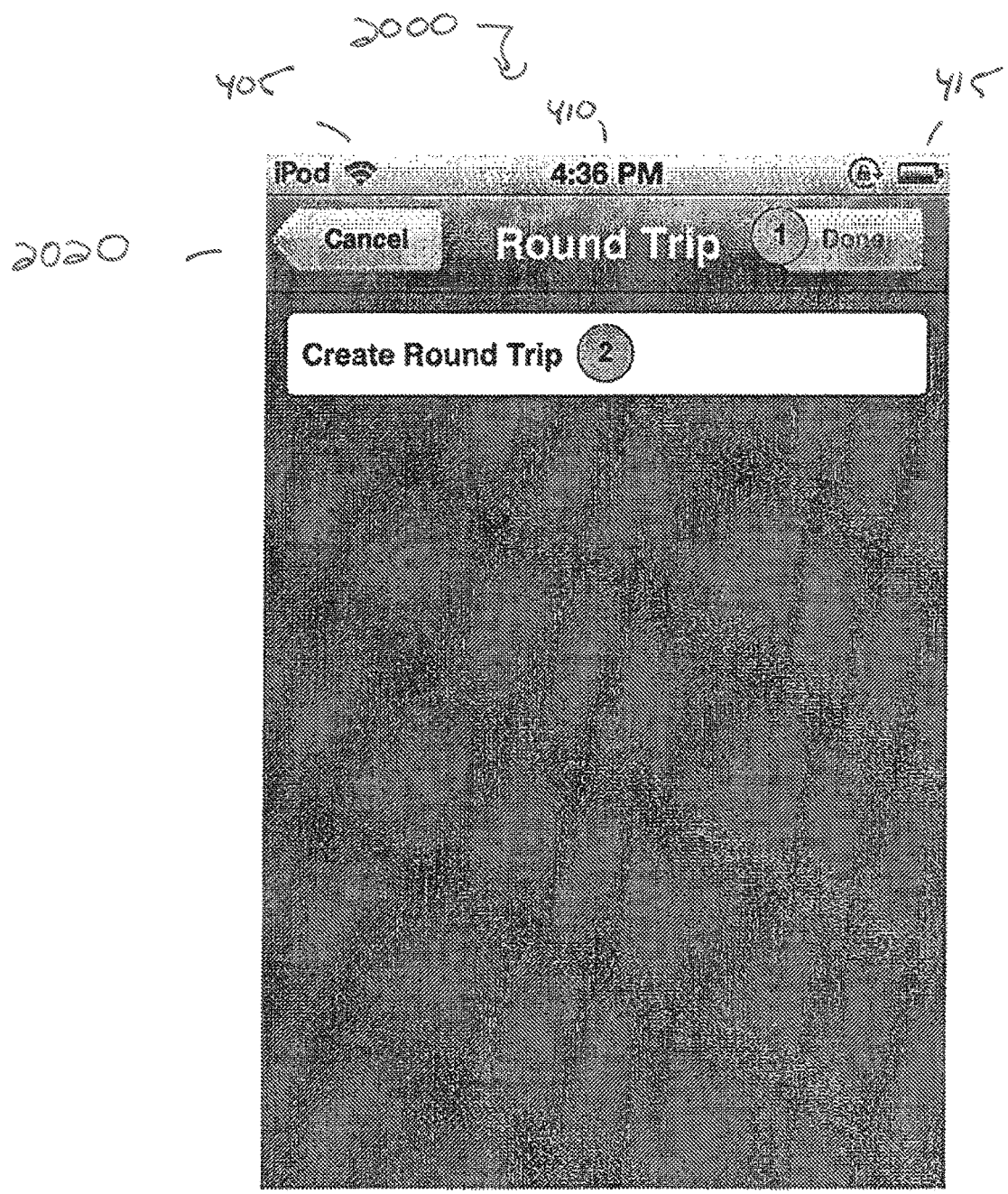
FIG. 20 illustrates an exemplary user interface by which a transporter may create and go in progress with a round trip job in some embodiments.

FIG. 20 illustrates an exemplary user interface to a Transport Management System by which a transporter may create and go in progress with a round trip job in some embodiments. In some embodiments, user interface 2000 includes the following elements, or a subset or superset thereof: 405, 410, 415, a described above; vertical area 2020, which contains a label identifying the screen being displayed (Round Trip) and an indication of where a user may press to return to the previous message screen or conclude interaction with the current screen. Figure reference 1 indicates a button which is only enabled if the user has selected create round trip in the screen. Upon touch, the current in progress job is completed, a new job to the patient's home location (i.e., point from which the trip originated) is created, and the user is put into dispatched status with a new job. It is preferred that the processing and retrieving new job screens are shown after the done button is selected. Then the user will be presented with the newly created job details. Figure reference 2 indicates a button which is selected upon touch and a checkmark will appear if the button is selected.

Figure 21:
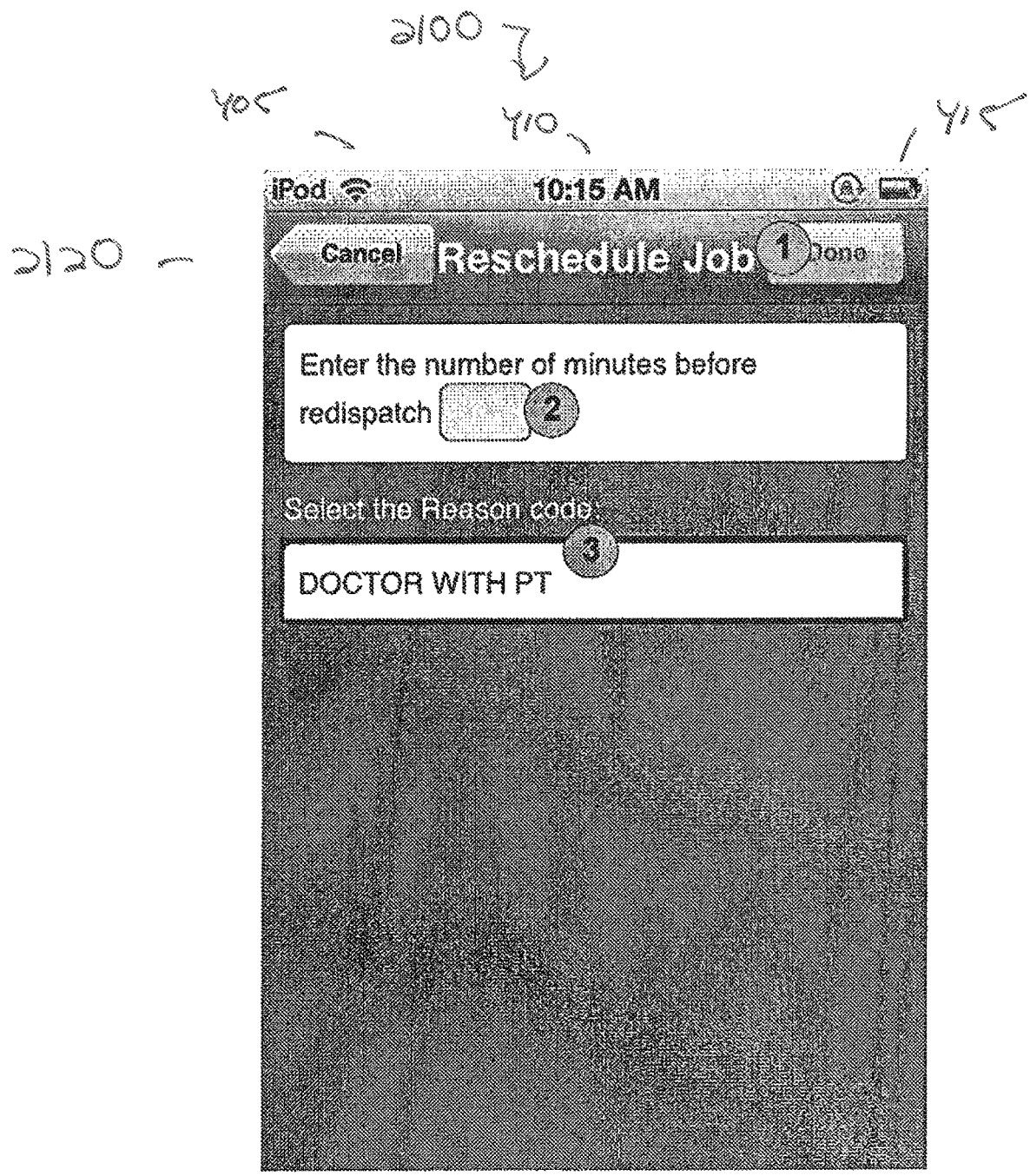
FIG. 21 illustrates an exemplary user interface by which a transporter may reschedule a job the transporter is dispatched or in progress on in some embodiments.

FIG. 21 illustrates an exemplary user interface to a Transport Management System by which a transporter may reschedule a job the transporter is dispatched or in progress on in some embodiments. In some embodiments, user interface 2100 (for reschedule job) includes the following elements, or a subset or superset thereof: 405, 410, 415, a described above; and vertical area 2020, which contains a label identifying the screen being displayed (Reschedule Job) and an indications of where a user may press to return to the previous message screen or conclude with the present screen. Figure reference 1 indicates a button which is only enabled if the user has entered a value of minutes before redispatch and selected a reason code, if one is required. Upon touch, the job is rescheduled for the time interval specified. It is preferred that the processing and retrieving new job screens are shown after selecting done. The user will then be presented with a new job, if there are no available jobs, navigation will be to the home screen. Figure reference indicates a text box where a user enters the number of minutes that will pass before the job is redispatched. This must be a whole number and if the value is less than the lead time for the origin location it is preferred that a warning be displayed to the user. Figure reference 3 indicates a list from which a reason code for the rescheduling may be selected. Although only one reason code is shown, there may be additional codes displayed. This only visible if it is predetermined to require same.

Figure 22:
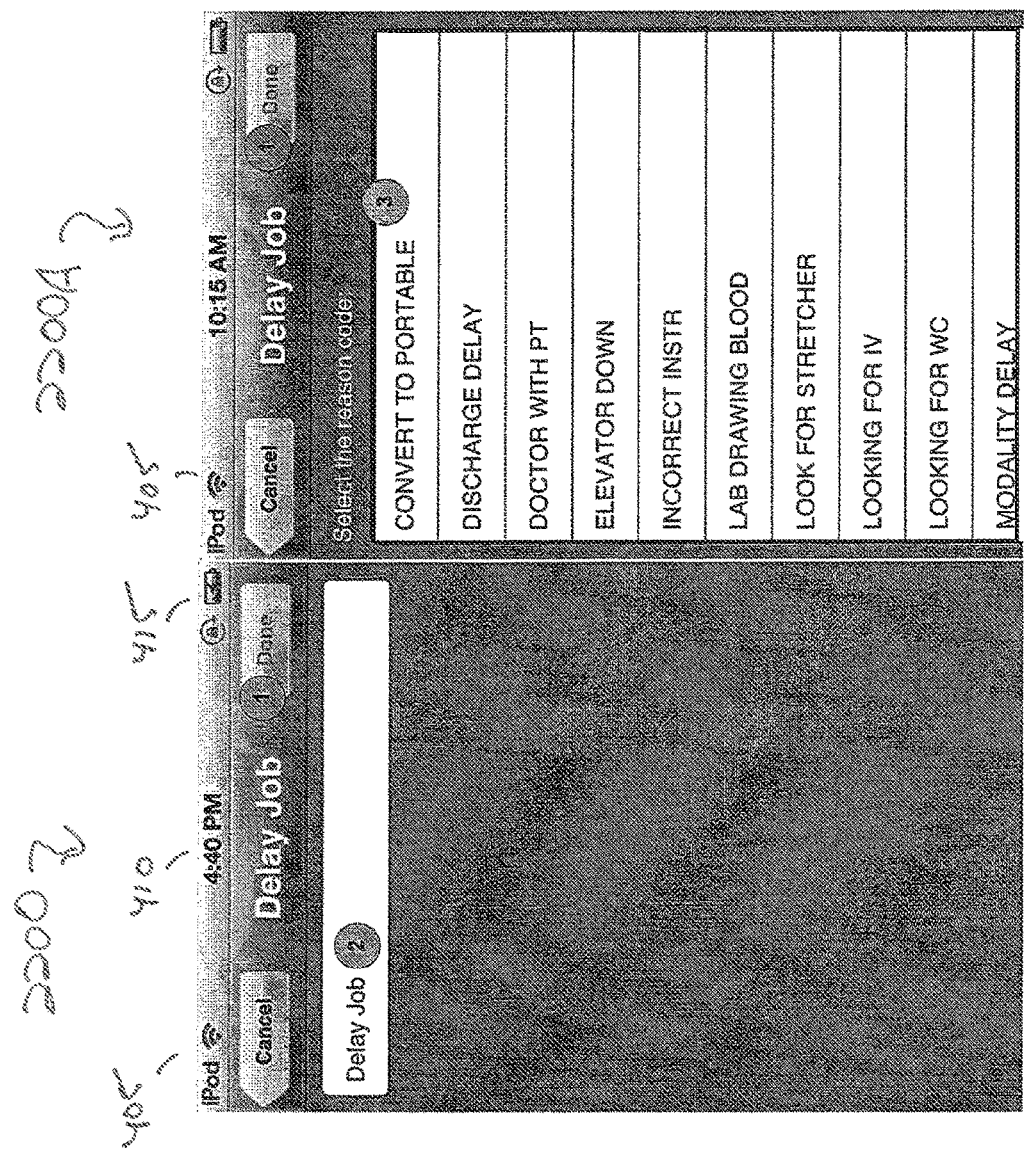
FIG. 22 illustrates an exemplary user interface by which a transporter may delay a job the transporter is dispatched or in progress on in some embodiments.

FIG. 22 illustrates an exemplary user interface to a Transport Management System by which a transporter may delay a job the transporter is dispatched or in progress on in some embodiments. In some embodiments, user interface 2200 (no reason code required) includes the following elements, or a subset or superset thereof: 405, 410, 415, a described above; and vertical area 2220, which contains a label identifying the screen being displayed (Delay Job) and an indications of where a user may press to return to the previous message screen or complete the task. Figure reference 1 indicates a button which is only enabled if the user has selected delay job in the interface or a reason code (see interface 2200A), if one is required. Upon touch, the button delays the current job. It is preferred that the processing screen is shown after selecting the button and the user will then be presented with the job details of the delayed job.

In some embodiments, user interface 2200A (reason code required) includes the following elements, or a subset or superset thereof: 405, 410, 415, a described above; and vertical area 2220A, which contains a label identifying the screen being displayed (Delay Job) and indications of where a user may press to cancel and return to the previous message screen or when the user is completed with the current screen. Figure reference 3 indicates a list which displays reason codes pre-determined by the hospital which a user may chose. This list will only be displayed if required for a particular user. The reason is selected by touching it and a checkmark will appear to indicate selection.

Figure 23:
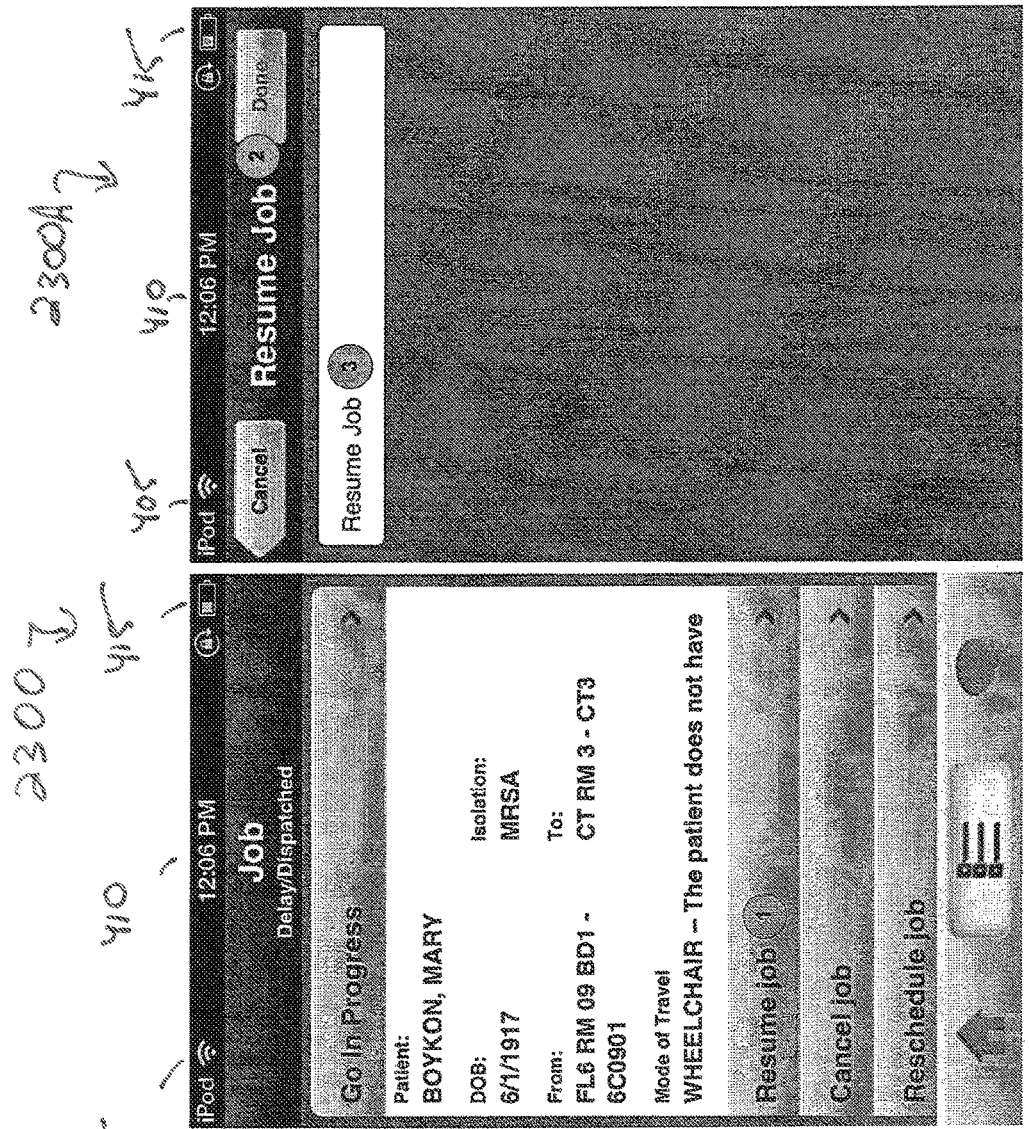
FIG. 23 illustrates an exemplary user interface by which a transporter may resume a job which the transporter previously delayed in some embodiments.

FIG. 23 illustrates an exemplary user interface to a Transport Management System by which a transporter may resume a job which the transporter previously delayed in some embodiments. In some embodiments, user interface 2300 includes the following elements, or a subset or superset thereof: 405, 410, 415, a described above; vertical area 2320, which contains a label identifying the screen being displayed (Job Delayed Dispatch); and vertical area 2325 which provides short cuts to some of the more frequently accessed tasks and, as shown, indicates the task being viewed (Joblist). Also displayed in the interface are job details and buttons for go in progress for accepting the job, resume job, cancel job, and reschedule job. Figure reference 1 indicates a button for resume job, which replaces the delay job button for a job that the user has delayed. Upon touch, the action is to navigate to the resume job screen (interface 2300A).

In some embodiments, user interface 2300A includes the following elements, or a subset or superset thereof: 405, 410, 415, a described above; and vertical area 2220A, which contains a label identifying the screen being displayed (Resume Job) and indications of where a user may press to cancel and return to the previous message screen or when the user is completed with the current screen. Figure reference 2 indicates a button which is only enabled if a user has selected resume job in the screen and upon touch, the delay from the current job is removed and the user status is changed to reflect the transporter has been dispatched. It is preferred that the processing screen is shown after done is selected and then the user will be presented with the job details. Figure reference 3 indicates a button for resume job, which upon touch it is selected and a checkmark will appear once selected.

Figure 24:
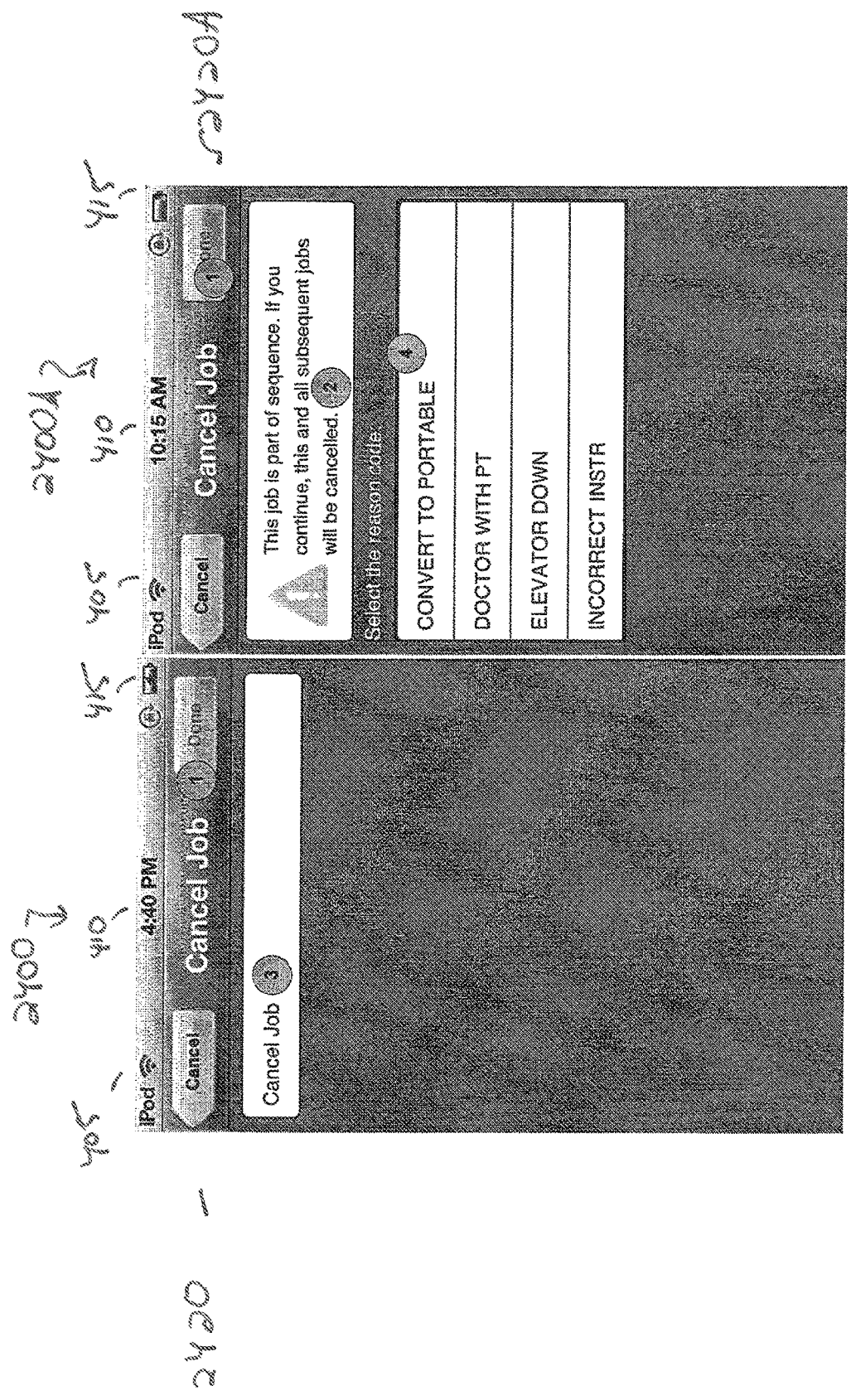
FIG. 24 illustrates another exemplary user interface by which a transporter may cancel a job the transporter is dispatched or in progress on in some embodiments.

FIG. 24 illustrates an exemplary user interface to a Transport Management System by which a transporter may cancel a job the transporter is dispatched or in progress on in some embodiments. In some embodiments, user interface 2400 includes the following elements, or a subset or superset thereof: 405, 410, 415, a described above; and vertical area 2420, which contains a label identifying the screen being displayed (Cancel Job) and an indication of where a user may press to return to the previous message screen or if done with the present screen. Figure reference 1 indicates a done button and is only enabled if the user as selected to cancel the job or selected a reason code (see interface 2400A), if one is required. Upon touch, the job is canceled. The processing and retrieving next job screens are shown after selecting done. The user will then be presented with a new job. If there are no available new jobs, navigation is to the home screen. Figure reference 3 indicates a cancel job button which will be displayed if a user is not required to enter a reason for the cancellation. This is selected by touch and a checkmark will appear once selected.

In some embodiments, user interface 2400A includes the following elements, or a subset or superset thereof: 405, 410, 415, as described above; and vertical area 2420A, which contains a label identifying the screen being displayed (Cancel Job) and an indication of where a user may press to return to the previous message screen or if done with the present screen. Figure reference 1 indicates a done button and is only enabled if the user as selected to cancel the job or selected a reason code (see interface 2400A), if one is required. Upon touch, the job is canceled. The processing and retrieving next job screens are shown after selecting done. The user will then be presented with a new job. If there are no available new jobs, navigation is to the home screen. Figure reference 2 indicates a warning label which provides information about the consequences of cancelling the job. Figure reference 4 indicates a list which displays reason codes pre-determined by the hospital to be valid reasons for cancelling a job. This list will only be displayed if a user is required to enter a reason code. Selection is by touch and once selected a checkmark will appear to indicate selection.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider) or through a hard wire connection, such as over a USB connection.

Aspects are described herein with reference to the figures, which illustrate example methods, devices and program products according to various example embodiments. It will be understood that the actions and functionality illustrated may be implemented at least in part by program instructions. These program instructions may be provided to a processor of a general purpose information handling device, a special purpose information handling device, or other programmable data processing device or information handling device to produce a machine, such that the instructions, which execute via a processor of the device implement the functions/acts specified.

The program instructions may also be stored in a device readable medium that can direct a device to function in a particular manner, such that the instructions stored in the device readable medium produce an article of manufacture including instructions which implement the functions/acts specified.

The program instructions may also be loaded onto a device to cause a series of operational steps to be performed on the device to produce a device implemented process such that the instructions which execute on the device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
at an application of a handheld portable information handling device of a transporter, wherein the application displays a plurality of user interfaces, each of the plurality of user interfaces having a subset of information corresponding to a hospital transport management system, wherein the application communicates information with the hospital transport management system:
communicating, to the hospital transport management system, information sufficient to authenticate the transporter within the hospital transport management system, wherein, upon authentication, the application displays the plurality of user interfaces of the hospital transport management system at the handheld portable information handling device and allows the transporter to interact with the plurality of user interfaces of the hospital transport management system;
obtaining, from the hospital transport management system and responsive to authenticating the transporter, available hospital transport job information from the hospital transport management system comprising information for all available transport jobs;
identifying a current status of the transporter, wherein the current status comprises a status selected from the group consisting of: in progress with a job, available, and on break;
displaying, to the transporter within one of the plurality of interfaces and responsive to identifying the current status as on break, a return to work icon;
displaying, to the transporter within one of the plurality of interfaces and responsive to identifying the current status as in progress with a job, details of the job; and
displaying, to the transporter within a different one of the plurality of interfaces and responsive to identifying the current status as available, the available hospital transport job information for a subset of the all available transport jobs, wherein the subset comprises hospital transport job information for transport jobs available to the transporter identified based upon an authority of the transporter;
receiving, from the transporter within the different one of the plurality of interfaces, a selection of one of the available hospital transport jobs;
displaying, within one of the plurality of interfaces viewable by the transporter, information related to the available hospital transport job selected by the transporter, wherein the information comprises information identifying requirements and attributes of the available hospital transport job;
displaying, within one of the plurality of interfaces viewable by the transporter, functional display icons comprising an accept job icon corresponding to the available hospital transport job selected by the transporter;

communicating, in response to the transporter interacting with the accept job icon, acceptance information of the authenticated transporter for an available hospital transport job to the hospital transport management system, wherein the hospital transport management system modifies details of the available hospital transport job within the hospital transport management system upon receipt of the acceptance information, the modified details being viewable by other users of the hospital transport management system; and displaying, within one of the plurality of interfaces and to the transporter, a status of the accepted job, details of the accepted job, and icons for changing a status of the accepted job by the transporter and interactive icons associated with the accepted job for interaction by the transporter.

2. The method of claim 1, wherein the information that is being displayed on the handheld portable information handling device comprises job requests and messages.

3. The method of claim 2, wherein additional information is displayed to the authenticated user of the handheld portable information handling device if the authenticated user selects a display element.

4. The method of claim 3, wherein the additional information for a job request includes the location of a patient to be transported.

5. The method of claim 4, wherein the additional information for a job request further includes the location to which the patient is to be transported.

6. The method of claim 1, further comprising displaying a bar for a predetermined amount of time, wherein the bar includes links to the authenticated user's home configuration, job list, and messages.

7. The method of claim 1, wherein displaying the available hospital transport job information comprises displaying tasks which are available for the authenticated user of the of the handheld portable information handling device to complete.

8. The method of claim 1, wherein the acceptance information comprises information indicating that the authenticated user of the handheld portable information handling device has completed a task.

9. A portable handheld information handling device, comprising:
one or more processors;
an application displaying a plurality of user interfaces, each of the plurality of user interfaces having a subset of information corresponding to a hospital transport management system, wherein the application communicates information with the hospital transport management system;
a memory operatively coupled to the one or more processors that stores instructions executable by the one or more processors to perform acts comprising:
communicating, to the hospital transport management system, information sufficient to authenticate a the transporter corresponding to the handheld portable information handling device within the hospital transport management system, wherein, upon authentication, the application displays the plurality of user interfaces of the hospital transport management system at the handheld portable information handling device and allows the transporter to interact with the plurality of user interfaces of the hospital transport management system;

obtaining, from the hospital transport management system and responsive to authenticating the transporter, available hospital transport job information from the hospital transport management system comprising information for all available transport jobs;
identifying a current status of the transporter, wherein the current status comprises a status selected from the group consisting of: in progress with a job, available, and on break;
displaying, to the transporter within one of the plurality of interfaces and responsive to identifying the current status as on break, a return to work icon;
displaying, to the transporter within one of the plurality of interfaces and responsive to identifying the current status as in progress with a job, details of the job; and
displaying, to the transporter within a different one of the plurality of interfaces and responsive to identifying the current status as available, the available hospital transport job information for a subset of the all available transport jobs, wherein the subset comprises hospital transport job information for transport jobs available to the transporter identified based upon an authority of the transporter;
receiving, from the transporter within the different one of the plurality of interfaces, a selection of one of the available hospital transport jobs;
displaying, within one of the plurality of interfaces viewable by the transporter, information related to the available hospital transport job selected by the transporter, wherein the information comprises information identifying requirements and attributes of the available hospital transport job;
displaying, within one of the plurality of interfaces viewable by the transporter, functional display icons comprising an accept job icon corresponding to the available hospital transport job selected by the transporter;
communicating, in response to the transporter interacting with the accept job icon, acceptance information of the authenticated transporter for an available hospital transport job to the hospital transport management system, wherein the hospital transport management system modifies details of the available hospital transport job within the hospital transport management system upon receipt of the acceptance information, the modified details being viewable by other users of the hospital transport management system; and
displaying, within one of the plurality of interfaces and to the transporter, a status of the accepted job, details of the accepted job, and icons for changing a status of the accepted job by the transporter and interactive icons associated with the accepted job for interaction by the transporter.

10. The apparatus of claim 9, wherein the information that is being displayed on the handheld portable information handling device comprises job requests and messages.

11. The apparatus of claim 9, wherein additional information is displayed to the authenticated user of the handheld portable information handling device if the authenticated user selects a display element.

12. The apparatus of claim 11, wherein the additional information for a job request includes the location of a patient to be transported.

13. The apparatus of claim 12, wherein the additional information for a job request further includes the location to which the patient is to be transported.

14. The apparatus of claim 9, further comprising instruction for displaying a bar for a predetermined amount of time, wherein the bar includes links to the authenticated user's home configuration, joblist, and messages.

15. The apparatus of claim 9, wherein displaying the available hospital transport job information comprises displaying tasks which are available for the authenticated user of the of the handheld portable information handling device to complete.

16. The apparatus of claim 9, wherein the acceptance information comprises information indicating that the authenticated user of the handheld portable information handling device has completed a task.

17. A program product, comprising:
   a non-transitory storage device encoded with computer program code, the computer program code being executable by a processor and comprising:
   computer program code configured to provide an application at a handheld portable information handling device of a transporter, wherein the application displays a plurality of user interfaces, each of the plurality of user interfaces having a subset of information corresponding to a hospital transport management system, wherein the application communicates information with the hospital transport management system using:
   computer program code configured to communicate to the hospital transport management system, information sufficient to authenticate the transporter within the hospital transport management system, wherein the handheld portable information handling device comprises a touch screen display and an application displaying a plurality of user interfaces, each of the plurality of user interfaces having a subset of information corresponding to a hospital transport management system, wherein, upon authentication, the application displays the plurality of user interfaces of the hospital transport management system at the handheld portable information handling device and allows the transporter to interact with the plurality of user interfaces of the hospital transport management system;
   computer readable program code configured to obtain, from the hospital transport management system and responsive to authenticating the transporter, available hospital transport job information from the hospital transport management system comprising information for all available transport jobs;
   computer readable program code configured to identify a current status of the transporter, wherein the current status comprises a status selected from the group consisting of: in progress with a job, available, and on break;
      computer readable program code configured to display, to the transporter within one of the plurality of interfaces and responsive to identifying the current status as on break, a return to work icon;
   computer readable program code configured to display, to the transporter within one of the plurality of interfaces and responsive to identifying the current status as in progress with a job, details of the job; and
   computer readable program code configured to display, to the transporter within a different one of the plurality of interfaces and responsive to identifying the current status as available, the available hospital transport job information for a subset of the all available transport jobs, wherein the subset comprises hospital transport job information for transport jobs available to the transporter identified based upon an authority of the transporter;
   computer readable program code configured to receive, from the transporter within the different one of the plurality of interfaces, a selection of one of the available hospital transport jobs;
   computer readable program code configured to display, within one of the plurality of interfaces viewable by the transporter, information related to the available hospital transport job selected by the transporter, wherein the information comprises information identifying requirements and attributes of the available hospital transport job;
   computer readable program code configured to display, within one of the plurality of interfaces viewable by the transporter, functional display icons comprising an accept job icon corresponding to the available hospital transport job selected by the transporter;
   computer readable program code configured to communicate, in response to the transporter interacting with the accept job icon, acceptance information of the authenticated transporter for an available hospital transport job to the hospital transport management system, wherein the hospital transport management system modifies details of the available hospital transport job within the hospital transport management system upon receipt of the acceptance information, the modified details being viewable by other users of the hospital transport management system; and
   computer readable program code configured to display, within one of the plurality of interfaces and to the transporter, a status of the accepted job, details of the accepted job, and icons for changing a status of the accepted job by the transporter and interactive icons associated with the accepted job for interaction by the transporter.

\* \* \* \* \*